(12) United States Patent
Bacher et al.

(10) Patent No.: US 7,364,853 B2
(45) Date of Patent: *Apr. 29, 2008

(54) DETECTION OF MICROSATELLITE INSTABILITY AND ITS USE IN DIAGNOSIS OF TUMORS

(75) Inventors: Jeffery W. Bacher, Madison, WI (US); Laura Flanagan, Fort Atkinson, WI (US); Nadine Nassif, Madison, WI (US)

(73) Assignee: Promega Corporation, Madison, WI (US)

( * ) Notice: Subject to any disclaimer, the term of this patent is extended or adjusted under 35 U.S.C. 154(b) by 272 days.

This patent is subject to a terminal disclaimer.

(21) Appl. No.: 11/037,321

(22) Filed: Jan. 18, 2005

(65) Prior Publication Data

US 2005/0202473 A1    Sep. 15, 2005

Related U.S. Application Data

(63) Continuation of application No. 09/663,020, filed on Sep. 15, 2000, now Pat. No. 6,844,152.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.33
(58) Field of Classification Search .................. 435/6, 435/91.2; 536/24.33
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 5,492,808 A | 2/1996 | de la Chapelle et al. | |
| 5,569,753 A | 10/1996 | Wigler et al. | |
| 5,578,450 A | 11/1996 | Thibodeau et al. | |
| 5,591,826 A | 1/1997 | de la Chapelle et al. | |
| 5,645,995 A | 7/1997 | Kieback | |
| 5,693,470 A | 12/1997 | de la Chapelle et al. | |
| 5,736,365 A | 4/1998 | Walker et al. | |
| 5,837,443 A | 11/1998 | de la Chapelle et al. | |
| 5,843,660 A | 12/1998 | Schumm et al. | |
| 5,843,757 A | 12/1998 | Vogelstein et al. | |
| 5,856,094 A | 1/1999 | Sidransky et al. | |
| 5,866,323 A | 2/1999 | Markowitz et al. | |
| 5,871,925 A | 2/1999 | de la Chapelle et al. | |
| 5,874,217 A | 2/1999 | Halverson et al. | |
| 5,912,147 A | 6/1999 | Stoler et al. | |
| 5,922,855 A | 7/1999 | Liskay et al. | |
| 5,935,787 A | 8/1999 | Sidransky | |
| 5,952,170 A | 9/1999 | Stroun et al. | |
| 6,090,558 A * | 7/2000 | Butler et al. ............. 435/6 |
| 6,150,100 A | 11/2000 | Ruschoff et al. | |
| 6,280,947 B1 | 8/2001 | Shuber et al. | |
| 6,331,393 B1 | 12/2001 | Laird et al. | |
| 6,531,282 B1 * | 3/2003 | Dau et al. ............. 435/6 |
| 6,844,152 B1 * | 1/2005 | Bacher et al. ............. 435/6 |
| 2003/0180758 A1 * | 9/2003 | Bacher et al. ............. 435/6 |

FOREIGN PATENT DOCUMENTS

| | | |
|---|---|---|
| EP | 0 869 188 A2 | 10/1998 |
| WO | WO 94/11531 | 5/1994 |
| WO | WO 95/15400 | 6/1995 |
| WO | WO 96/06951 | 3/1996 |
| WO | WO 98/08980 | 3/1998 |
| WO | WO 00/09759 | 2/2000 |
| WO | WO 02/22879 | 3/2002 |

OTHER PUBLICATIONS

Frazier et al. Loci for efficient detection of microsatellite instability in hereditary non-polyposis coloraectal cancer. Oncology Reports, vol. 6, pp. 497-505, 1999.*
Schroer KP et al. Analysis of the co-amplified STR loci D1S1656, D12S391 and D18S51: population data and validation study for a highly discriminating triplex-PCR. Forensic Science International, vol. 113, pp. 17-20, Sep. 11, 2000.*
Samowitz et al. BAT-26 and BAT-40 instability in colorectal adenomas and carcinomas and germline polymorphisms. American J Pathology, vol. 154, No. 6, pp. 16371641, 1999.*
Bacher, J. et al., "Fluorescent Multiplex PCT System for Detection of Microsatellite Instability," Cancer Research (2001) 42:750.
Samowitz, W. et al., "BAT-26 and BAT-40 Instability in Colorectal Adenomas and Carcinomas and Germline Polymorphisms," Amer. J. Pathology (1999) 154(6):1637-1641.
Sulston, J.E. et al. *Genome Res*, Toward a complete human genome sequence. 1998 vol. 8, No. 11, 1097-1108.
Loeb L. A. Microsatellite instability: marker of a mutator phenotype in cancer. Cancer Res., 54: 5059-5063, 1994.
Loeb, L. A., Cancer cells exhibit a mutator phenotype. Adv Cancer Res. 1998;72:25-56.
Rodriquez-Bigas, Miguel A., et al., A National Cancer Institute Workshop on Hereditary Nonpolyposis colorectal Cancer Syndrome: Meeting Highlights and Bethesda Guidelines, Journal of the National Cancer Institute, Dec. 3, 1997, vol. 89, No. 23, 1758-1762.
Aaltonen, Lauri A., et al., Incidence of Hereditary Nonplyposis Colorectal Cancer and the Feasiblity of Molecular Screening for the Disease, The New England Journal of Medicine, 1998, vol. 338, No. 21, 1481-1487.
Edelmann, Winfried, et al., The DNA Mismatch Repair Genes Msh3 and Msh6 Cooperate in Intestinal Tumor Suppression, J. Cancer Research, 60, 803-807, Feb. 15, 2000.

(Continued)

*Primary Examiner*—Suryaprabha Chunduru
(74) *Attorney, Agent, or Firm*—Michael Best & Friedrich LLP

(57) ABSTRACT

Methods and kits are disclosed for use in the analysis of microsatellite instability in genomic DNA. Methods and kits are also disclosed which can be used to detect microsatellite instability DNA present in biological materials, such as tumors. The methods and kits of the present invention can be used to detect or diagnose diseases associated with microsatellite instability, such as certain types of cancer.

7 Claims, 13 Drawing Sheets

OTHER PUBLICATIONS

Karnes, William E., et al., Reduced COX-2 Protein in Colorectal Cancer with Defective Mismatch Repair, J. Cancer Research 58, 5473-5477, Dec. 1, 1998.
Duddy, Steven K., et al., Genetic Analysis of Multiple Loci in Microsamples of Fixed Paraffin-Embedded Tissue, Toxicological Sciences 46, 317-323 (1998).
Liu, Tao, et al., Microsatellite Instability as a Predictor of a Mutation in a DNA Mismatch Repair Gene in Familial Colorectal Cancer, Genes, Chromosomes & Cancer, 27:17-25 (2000).
Loktionov, A., et al., Quantitation of DNA from Exfoliated Colonocytes Isolated from Human Stool Surface as a Novel Noninvasive Screening Test for Colorectal Cancer, Clin Cancer Res., 4(2):337-42 Feb. 1998 (Abstract).
Boland, C. Richard, Setting Microsatellites Free, Nature Medicine, vol. 2, No. 9, Sep. 1996, 972-974.
Salahshor, Sima, Colorectal Cancer With and Without Microsatellite Instability Involves Different Genes, Genes, Chromosomes & Cancer, 26:247-252 (1999).
Marra, Giancarlo, et al., Hereditary Nonpolyposis Colorectal Cancer: the Syndrome, the Genes, and Historical Perspectives, Journal of the National Cancer Institute, vol. 87, No. 15, Aug. 2, 1995, 1114-1125.
Horii, Akira, et al., Frequent Replication Errors at Microsatellite Loci in Tumors of Patients with Multiple Primary Cancers, Cancer Research 54, 3372-3375, Jul. 1, 1994.
Peltomaki, Paivi, DNA Mismatch Repair Gene Mutations in Human Cancer, Environmental Health Perspectives, vol. 105, Suppl. 4, Jun. 1997, 775-780.
Perucho, Manuel, Microsatellite Instability: The Mutator that Mutates the Other Mutator, Nature Medicine, vol. 2, No. 6, Jun. 1996, 630-631.
Eshleman, James R., et al., Mismatch Repair Defects in Human Carcinogenesis, Human Molecular Genetics, 1996 Oxford University Press, vol. 5, Review, 1489-1494.
Lothe, Ragnhild A., Microsatellite Instability in Human Solid Tumors, Molecular Medical Today, Feb. 1997, 61-68.
Faquin WC, Fitzgerald JT, Lin MC, Boynton KA, Muto MG, Mutter GL. Sporadic microsatellite instability is specific to nepotistic and preneoplastic endometrial tissues. Am J Clin Pathol 2000; 113(4):576-582.
Kiriu, Hiroshi, et al., Microsatellite instability associated with primary head and neck cancers and secondary esophageal cancers, Jpn J Clin Oncol. Dec. 1998;28(12):733-9.
Stone, J.G., et al., Optimising methods for determining RER status in colorectal cancers, Cancer Letters 149 (2000) 15-20.
Kuska, B., New Diagnostic Criteria for HNPCC Are On the Way, Journal of the National Cancer Institute, vol. 89, No. 1, Jan. 1, 1997, 11-12.
Segev, Dorry L., et al., Polymerase Chain Reaction-Based Microsatellite Polymorphism Analysis of Follicular and Hürthle Cell Neoplasms of the Thyroid, The Journal of Clinical Endocrinology & Metabolism, vol. 83, No. 6 2036-2042 (1998).
Dietmaier, W., et al., Detection of Microsatellite Instability (MSI) and Loss of Heterozygosity (LOH) in Colorectal Tumors by Fluorescence-based Multiplex Microsatellite PCR, Roche Molecular Biochemicals, Biochemica, No. 2, 1999, 42-45.
Huber, P., et al., Random Priming and Multiplex PCR with Three Short Tandem Repeats for Forensic Casework, Fourth International Symposium on Human Identification (1993), pp. 220.
Slebos, R.J.C. et al., "Mutations in tetranucleotide repeats following DNA damage depend on repeat sequence and carcinogenic agent," Cancer Res. (2002) 62:6052-6060.
Pyatt, R. et al., "Polymorphic variation at the BAT-25 and BAT-26 loci in individuals of African origin," Am. J. Path. (1999) 155(2):349-353.
Contente, A. et al., "A polymorphic microsatellite that mediates induction of PIG3 by p53," Nature Genetics (2002) 30:315-320.
Aaltonen et al., 1993, Science 260:812-815.
Altschul, et al. 1990 J. Mol. Biol. 215:403-410.
AmpFISTR COfiler™ PCR Amplification Kit User Bulletin (1998), i-iii and 1-1 to 1-10, published by Perkin-Elmer Corp.
AmpFISTR Profiler™ PCR Amplification Kit User's Manual (1997), i-viii and 1-1 to 1-10; published by Perkin-Elmer Corp.
Anker et al., 1997 Gastroenterology 112:1114-1120.
Bacher & Schumm, 1998 Profiles in DNA 2:3-6.
Bacher, J. et al., Proceedings of the American Association for Cancer Research Annual, Mar. 2001, vol. 42, 750.
Berg, et al., "Detection of Microsatellite Instability by Fluorescence Multiplex Polymerase Chain Reaction", J. Molecular Diagnostics, 2000, 2(1):20-28.
Bertario et al., 1999 International J Cancer 80:183-187.
Boland, 1998 Cancer Res 58:5248-5257.
Brinkman, et al., 1998 Am. J. Genet., 62:1408-1415.
Bronner et al., 1994 Nature 368:258-61.
Calin, et al., "Genetic Progression in Microsatellite Instability High (MSI-H) Colon Cancers Correlates with Clinico-Pathological Parameters: A Study of the TGF βRII, BAX, HMSH3, HMSH6 and BLM Genes" Int. J. Cancer, 89, 230-235 (2000).
Chakraborty, et al., 1997 Proc. Natl. Acad. Sci. 94:1041-1046.
Chen et al., 1996 Nature Medicine 2(3):1033-1035.
Chen et al., 1999 Clinical Cancer Res 5:2297-2303.
Chong et al., 1994 Cancer Res 54:4595-4597.
Dietmaier et al., 1997 Cancer Res 57:4749-4756.
Duval, et al., "Evolution of Instability at Coding and Non-Coding Repeat Sequences in Human MSI-H Colorectal Cancers" Human Molecular Genetics, 10(5): 513-518 (2001).
Fishel et al., 1993 Cell 75:1027-38.
Fleisher, A.S., et al., Cancer Research, Sep. 1, 2000, vol. 60, No. 17, 4864-4868.
Frazier et al., 1999 Oncology Reports 6:497-505.
Frazier, et al., "Loci for efficient detection of microsatellite instability in hereditary non-polyposis colorectal cancer", Oncology Reports, 1999, 6:497-505.
Fujiwara et al., 1999 Cancer Res 59:1567-1571.
Gao et al., 1994 Oncogene 9:2999-3003.
Ghoussein et al., 1999 Clinical Cancer Res 5:1950-1960.
Gibson, Sandra D. et al., Proceedings: American Academy of Forensic Sciences (Feb. 9-14, 1998) p. 53, B89.
Goessl et al., 1998 Cancer Res 58:4728-4732.
Gonzalez-Zulueta et al., 1993 Cancer Res 53:5620-23.
Grady et al., 1999 Cancer Res 59:320-324.
Han et al., 1993 Cancer Res 53:5087-5089.
Hibi, K. et al., 1998 Cancer Res 58:1405-1407.
Hoang et al., 1997 Cancer Res 57:300-303.
Ionov et al., 1993 Nature 363:558-561.
Kolodner et al., 1999 Cancer Res 59:5068:5074.
Kopreski et al., 1999 Clinical Cancer Res 5:1961-1965.
Kwoh, D. Y., and Kwoh, T. , 1990 J., American Biotechnology Laboratory, Oct. 14-25.
Lazaruk, Katherine et al., Proceedings: American Academy of Forensic Sciences (Feb. 9-14, 1998) p. 51, B83.
Leach et al., 1993 Cell 75:1215-1225.
Lee, et al., 1999 Human Molecular Genetics, 8(13) 2567-2572.
Leon et al., 1977 Cancer Res 37:646-650.
Levinson & Gutman, 1987 Molecular Biology Evolution 4(3):203-21.
Lindqvist, A.K., et al., Genome Research, United States Dec. 1996, vol. 6, No. 12, 1170-1176.
Liu et al., 1996 Nature Med 2,(2):169-174.
Lothe et al., 1993 Cancer Res. 53: 5849-5852.
Mao et al., 1996 PNAS 91:9871-9875.
Markowitz et al., 1995 Science 268:1336-1338.
Micka et al., 1999 Journal of Forensic Sciences 44(6):1243-1257.
Miozzo et al., 1996 Cancer Res 56:2285-2288.
Mironov et al., 1994 Cancer Res 54:41-44.
Miyaki et al., 1997 Nat Genetics 17:271-2.
Mori, et al., "Instabilotyping: Comprehensive Identification of Frameshift Mutations Caused by Coding Region Microsatellite Instability" Cancer Research, 61, 6046-6049 (Aug. 1, 2001).
Nawroz et al., 1996 Nature Med 2(9):1035-1037.
Nicolaides et al., 1994 Nature 371:75-80.
Papadopoulos et al., 1994 Science 263:1625-1629.
Parsons et al., 1995 Cancer Res 55:5548-5550.
Patel et al., 1994 Oncogene 9:3695-3700.

Peltomaki et al., 1993 *Cancer Res* 53:5853-5855.
Peltomaki et al., 1997 *Gastroenterologly* 113:1146-1158.
Perucho, M., 1999 *Cancer Res* 59:249-256.
Petes, et al., 1997 *Genetics*, 146: 491-498.
Planck et al., 2000 *Genes, Chromosomes & Cancer* 29:33-39.
Potočnik, et al,. 2000 *Eur J Physiol* 439 [Suppl]: R47-R-49.
Rhyu et al., 1994 *Oncogene* 9:29-32.
Risinger et al., 1993 *Cancer Res* 53:5100-5103.
Saiki, R. K., et al., 1985 *Science* 230: 1350-1354.
Samowitz, W., et al. *American Journal of Pathology*, United States Jun. 1999, vol. 154, No. 6, 1637-1641.
Schlotterer and Tautz, 1992 *Nucleic Acids Res* 20(2):211-15.
Schmitt, F.C. et al., *International Journal of Cancer*, Aug. 1999, vol. 82, No. 5, 644-647.
Schumm, James W. et al., *Proceedings: American Academy of Forensic Sciences* (Feb. 9-14, 1998), p. 53, B88.
Sia et al., 1997 *Molecular and Cellular Biology* 17(5):2851-2858.
Sorenson et al., 1994 *Cancer Epidemiol. Biomark. Prev.* 3:67-71.
Sorenson, G., 2000 *Clinical Cancer Res* 6:2129-2137.
Sparkes, R. et al., 1996 *Int J Legal Med* 109:186-194.
Stroun et al., 1989 *Oncology* 46:318-322.
Sutter, et al., "Molecular screening of potential HNPCC patients using a multiplex microsatellite PCT system", *Molecular and Cellular Probes*, 1999, 13:157-165.

Terdiman et al., 1999 *The American Journal of Gastroenterology* 94(9):2344-2356.
Thibodeau et al. 1998 *Cancer Res* 58, 1713-1718.
Thibodeau et al., 1993 *Science* 260:816-819.
Vasioukhin et al., 1994 *Br. J Haematol* 86: 774-779.
Walker, G. T., et al., 1992 *Proc. Natl. Acad. Sci., U.S.A.* 89: 392-396.
Wallin, J.M. et al., *Journal of Forensic Sciences*, Jul. 1998, vol. 43, No. 4, 854-870.
Weber and Wong, 1993 *Human Molecular Genetics* 2(8) 1123-1128.
Wijnen et al., 1999 *Nature Genetics* 23:142-144.
Wu et al., 1999, *Am J Hum Genetics* 65:1291-1298.
Yamamoto et al., 1998 *Cancer Res* 58:997-1003.
Zhang, et al., "Short Mononucleotide Repeat Sequence Variability in Mismatch Repair-deficient Cancers" *Cancer Research*, 61, 3801-3805 (May 1, 2001).
Zhou et al., 1998 *Genes, Chromosomes & Cancer* 21:101-107.
Zhou, et al., "Allelic Profiles of Mononucleotide Repeat Microsatellites in Control Individuals and in Colorectal Tumors with and without Replication Errors" *Oncogene* 15, 1713-1718, (1997).

* cited by examiner

SEQUENCE LISTING

```
<160> NUMBER OF SEQ ID NOS: 62

<210> SEQ ID NO 1
<211> LENGTH: 20
<212> TYPE: DNA
<213> ORGANISM: Homo sapiens
<220> FEATURE:
<223> OTHER INFORMATION: BAT-25 primer

<400> SEQUENCE: 1
tcgcctccaa gaatgtaagt                                             20

<210> SEQ ID NO 2
<211> LENGTH: 21
<212> TYPE: DNA
<213> ORGANISM: Homo sapiens
<220> FEATURE:
<223> OTHER INFORMATION: BAT-25 primer

<400> SEQUENCE: 2
tctgcatttt aactatggct c                                           21

<210> SEQ ID NO 3
<211> LENGTH: 21
<212> TYPE: DNA
<213> ORGANISM: Homo sapiens
<220> FEATURE:
<223> OTHER INFORMATION: BAT-26 primer

<400> SEQUENCE: 3
tgactacttt tgacttcagc c                                           21

<210> SEQ ID NO 4
<211> LENGTH: 22
<212> TYPE: DNA
<213> ORGANISM: Homo sapiens
<220> FEATURE:
<223> OTHER INFORMATION: BAT-26 primer

<400> SEQUENCE: 4
```
aaccattcaa cattttaac cc                                          22

<210> SEQ ID NO 5
<211> LENGTH: 20
<212> TYPE: DNA
<213> ORGANISM: Homo sapiens
<220> FEATURE:
<223> OTHER INFORMATION: MONO-11 primer

<400> SEQUENCE: 5
gagctgtgat tgcactacac                                            20

<210> SEQ ID NO 6
<211> LENGTH: 24
<212> TYPE: DNA
<213> ORGANISM: Homo sapiens
<220> FEATURE:
<223> OTHER INFORMATION: MONO-11 primer

<400> SEQUENCE: 6
ggcatgaatt actactgtcc tact                                       24

<210> SEQ ID NO 7
<211> LENGTH: 24
<212> TYPE: DNA
<213> ORGANISM: Homo sapiens
<220> FEATURE:
<223> OTHER INFORMATION: MONO-15 primer

<400> SEQUENCE: 7
tcagatttat tttgggcttc actc                                       24

<210> SEQ ID NO 8
<211> LENGTH: 18
<212> TYPE: DNA
<213> ORGANISM: Homo sapiens
<220> FEATURE:
<223> OTHER INFORMATION: MONO-15 primer

<400> SEQUENCE: 8
ggcggagctt gcagtgag                                              18

<210> SEQ ID NO 9
<211> LENGTH: 20
<212> TYPE: DNA
<213> ORGANISM: Homo sapiens
<220> FEATURE:
<223> OTHER INFORMATION: D1S518 primer

<400> SEQUENCE: 9
tgcagatctt gggacttctc                                            20

<210> SEQ ID NO 10
<211> LENGTH: 20
<212> TYPE: DNA
<213> ORGANISM: Homo sapiens
<220> FEATURE:
<223> OTHER INFORMATION: D1S518 primer

<400> SEQUENCE: 10
aaaaagagtg tgggcaactg                                            20

<210> SEQ ID NO 11
<211> LENGTH: 20
<212> TYPE: DNA

```
<213> ORGANISM: Homo sapiens
<220> FEATURE:
<223> OTHER INFORMATION: D1S547 primer

<400> SEQUENCE: 11
ctgaagtggg aggattgctt                                               20

<210> SEQ ID NO 12
<211> LENGTH: 20
<212> TYPE: DNA
<213> ORGANISM: Homo sapiens
<220> FEATURE:
<223> OTHER INFORMATION: D1S547 primer

<400> SEQUENCE: 12
aattcagggg agttccagag                                               20

<210> SEQ ID NO 13
<211> LENGTH: 20
<212> TYPE: DNA
<213> ORGANISM: Homo sapiens
<220> FEATURE:
<223> OTHER INFORMATION: D1S1677 primer

<400> SEQUENCE: 13
agtcagcttg attgacccag                                               20

<210> SEQ ID NO 14
<211> LENGTH: 21
<212> TYPE: DNA
<213> ORGANISM: Homo sapiens
<220> FEATURE:
<223> OTHER INFORMATION: D1S1677 primer

<400> SEQUENCE: 14
cttagtgtga caggaaggac g                                             21

<210> SEQ ID NO 15
<211> LENGTH: 20
<212> TYPE: DNA
<213> ORGANISM: Homo sapiens
<220> FEATURE:
<223> OTHER INFORMATION: D2S1790 primer

<400> SEQUENCE: 15
acatgtcgat ctcagcgttc                                               20

<210> SEQ ID NO 16
<211> LENGTH: 20
<212> TYPE: DNA
<213> ORGANISM: Homo sapiens
<220> FEATURE:
<223> OTHER INFORMATION: D2S1790 primer

<400> SEQUENCE: 16
gagttttatt ggccaaagca                                               20

<210> SEQ ID NO 17
<211> LENGTH: 20
<212> TYPE: DNA
<213> ORGANISM: Homo sapiens
<220> FEATURE:
<223> OTHER INFORMATION: D3S2432 primer

<400> SEQUENCE: 17
ggcaggcagg tagatagaca                                               20
```

<210> SEQ ID NO 18
<211> LENGTH: 23
<212> TYPE: DNA
<213> ORGANISM: Homo sapiens
<220> FEATURE:
<223> OTHER INFORMATION: D3S2432 primer

<400> SEQUENCE: 18
acactaaaca agcatagtca ggc                                    23

<210> SEQ ID NO 19
<211> LENGTH: 20
<212> TYPE: DNA
<213> ORGANISM: Homo sapiens
<220> FEATURE:
<223> OTHER INFORMATION: D5S818 primer

<400> SEQUENCE: 19
gggtgatttt cctctttggt                                        20

<210> SEQ ID NO 20
<211> LENGTH: 20
<212> TYPE: DNA
<213> ORGANISM: Homo sapiens
<220> FEATURE:
<223> OTHER INFORMATION: D5S818 primer

<400> SEQUENCE: 20
tgattccaat catagccaca                                        20

<210> SEQ ID NO 21
<211> LENGTH: 20
<212> TYPE: DNA
<213> ORGANISM: Homo sapiens
<220> FEATURE:
<223> OTHER INFORMATION: D5S2849 primer

<400> SEQUENCE: 21
cctggaagaa ccaatgctta                                        20

<210> SEQ ID NO 22
<211> LENGTH: 20
<212> TYPE: DNA
<213> ORGANISM: Homo sapiens
<220> FEATURE:
<223> OTHER INFORMATION: D5S2849 primer

<400> SEQUENCE: 22
ttgagcccag aaagtttgag                                        20

<210> SEQ ID NO 23
<211> LENGTH: 20
<212> TYPE: DNA
<213> ORGANISM: Homo sapiens
<220> FEATURE:
<223> OTHER INFORMATION: D6S1053 primer

<400> SEQUENCE: 23
tatttcaaag gcagcaaagc                                        20

<210> SEQ ID NO 24
<211> LENGTH: 20
<212> TYPE: DNA
<213> ORGANISM: Homo sapiens
<220> FEATURE:

<223> OTHER INFORMATION: D6S1053 primer

<400> SEQUENCE: 24
gcttgcagac agcctattgt                                       20

<210> SEQ ID NO 25
<211> LENGTH: 20
<212> TYPE: DNA
<213> ORGANISM: Homo sapiens
<220> FEATURE:
<223> OTHER INFORMATION: D7S1808 primer

<400> SEQUENCE: 25
cagaacaaac aaatggggag                                       20

<210> SEQ ID NO 26
<211> LENGTH: 20
<212> TYPE: DNA
<213> ORGANISM: Homo sapiens
<220> FEATURE:
<223> OTHER INFORMATION: D7S1808 primer

<400> SEQUENCE: 26
ccaaataaga ctcaggacgc                                       20

<210> SEQ ID NO 27
<211> LENGTH: 20
<212> TYPE: DNA
<213> ORGANISM: Homo sapiens
<220> FEATURE:
<223> OTHER INFORMATION: D7S3046 primer

<400> SEQUENCE: 27
acatacggat gaatggatgg                                       20

<210> SEQ ID NO 28
<211> LENGTH: 23
<212> TYPE: DNA
<213> ORGANISM: Homo sapiens
<220> FEATURE:
<223> OTHER INFORMATION: D7S3046 primer

<400> SEQUENCE: 28
tataacctct ctccctatct ccc                                   23

<210> SEQ ID NO 29
<211> LENGTH: 20
<212> TYPE: DNA
<213> ORGANISM: Homo sapiens
<220> FEATURE:
<223> OTHER INFORMATION: D7S3070 primer

<400> SEQUENCE: 29
cccccatgag ttattcctct                                       20

<210> SEQ ID NO 30
<211> LENGTH: 20
<212> TYPE: DNA
<213> ORGANISM: Homo sapiens
<220> FEATURE:
<223> OTHER INFORMATION: D7S3070 primer

<400> SEQUENCE: 30
ggaagccaaa tgttgaattg                                       20

```
<210> SEQ ID NO 31
<211> LENGTH: 25
<212> TYPE: DNA
<213> ORGANISM: Homo sapiens
<220> FEATURE:
<223> OTHER INFORMATION: D8S1179 primer

<400> SEQUENCE: 31
tttttgtatt tcatgtgtac attcg                                              25

<210> SEQ ID NO 32
<211> LENGTH: 25
<212> TYPE: DNA
<213> ORGANISM: Homo sapiens
<220> FEATURE:
<223> OTHER INFORMATION: D8S1179 primer

<400> SEQUENCE: 32
cgtagctata attagttcat tttca                                              25

<210> SEQ ID NO 33
<211> LENGTH: 20
<212> TYPE: DNA
<213> ORGANISM: Homo sapiens
<220> FEATURE:
<223> OTHER INFORMATION: D9S2169 primer

<400> SEQUENCE: 33
ttcccaaaag ttgccatcta                                                    20

<210> SEQ ID NO 34
<211> LENGTH: 20
<212> TYPE: DNA
<213> ORGANISM: Homo sapiens
<220> FEATURE:
<223> OTHER INFORMATION: D9S2169 primer

<400> SEQUENCE: 34
agcccaaaat gttatgcaag                                                    20

<210> SEQ ID NO 35
<211> LENGTH: 20
<212> TYPE: DNA
<213> ORGANISM: Homo sapiens
<220> FEATURE:
<223> OTHER INFORMATION: D10S1426 primer

<400> SEQUENCE: 35
ttggtggtgt catcctcttt                                                    20

<210> SEQ ID NO 36
<211> LENGTH: 20
<212> TYPE: DNA
<213> ORGANISM: Homo sapiens
<220> FEATURE:
<223> OTHER INFORMATION: D10S1426 primer

<400> SEQUENCE: 36
ctcttaactg atttggccga                                                    20

<210> SEQ ID NO 37
<211> LENGTH: 20
<212> TYPE: DNA
<213> ORGANISM: Homo sapiens
<220> FEATURE:
<223> OTHER INFORMATION: D10S2470 primer
```

```
<400> SEQUENCE: 37
cctcctagct cctcaagctt                                              20

<210> SEQ ID NO 38
<211> LENGTH: 20
<212> TYPE: DNA
<213> ORGANISM: Homo sapiens
<220> FEATURE:
<223> OTHER INFORMATION: D10S2470 primer

<400> SEQUENCE: 38
caggacagat ttcctgtggt                                              20

<210> SEQ ID NO 39
<211> LENGTH: 20
<212> TYPE: DNA
<213> ORGANISM: Homo sapiens
<220> FEATURE:
<223> OTHER INFORMATION: D12S391 primer

<400> SEQUENCE: 39
aacaggatca atggatgcat                                              20

<210> SEQ ID NO 40
<211> LENGTH: 20
<212> TYPE: DNA
<213> ORGANISM: Homo sapiens
<220> FEATURE:
<223> OTHER INFORMATION: D12S391 primer

<400> SEQUENCE: 40
tggcttttag acctggactg                                              20

<210> SEQ ID NO 41
<211> LENGTH: 20
<212> TYPE: DNA
<213> ORGANISM: Homo sapiens
<220> FEATURE:
<223> OTHER INFORMATION: D17S1294 primer

<400> SEQUENCE: 41
tggcatgcaa ttgtagtctc                                              20

<210> SEQ ID NO 42
<211> LENGTH: 25
<212> TYPE: DNA
<213> ORGANISM: Homo sapiens
<220> FEATURE:
<223> OTHER INFORMATION: D17S1294 primer

<400> SEQUENCE: 42
ttctttcctt actaagttga gaacg                                        25

<210> SEQ ID NO 43
<211> LENGTH: 20
<212> TYPE: DNA
<213> ORGANISM: Homo sapiens
<220> FEATURE:
<223> OTHER INFORMATION: D17S1299 primer

<400> SEQUENCE: 43
tagcacttga gcacacatgg                                              20

<210> SEQ ID NO 44
<211> LENGTH: 20
```

```
<212> TYPE: DNA
<213> ORGANISM: Homo sapiens
<220> FEATURE:
<223> OTHER INFORMATION: D17S1299 primer

<400> SEQUENCE: 44
gtgcattatg gggaccatta                                        20

<210> SEQ ID NO 45
<211> LENGTH: 20
<212> TYPE: DNA
<213> ORGANISM: Homo sapiens
<220> FEATURE:
<223> OTHER INFORMATION: D18S51 primer

<400> SEQUENCE: 45
gagccatgtt catgccactg                                        20

<210> SEQ ID NO 46
<211> LENGTH: 20
<212> TYPE: DNA
<213> ORGANISM: Homo sapiens
<220> FEATURE:
<223> OTHER INFORMATION: D18S51 primer

<400> SEQUENCE: 46
caaacccgac taccagcaac                                        20

<210> SEQ ID NO 47
<211> LENGTH: 21
<212> TYPE: DNA
<213> ORGANISM: Homo sapiens
<220> FEATURE:
<223> OTHER INFORMATION: FGA primer

<400> SEQUENCE: 47
ccataggttt tgaactcaca g                                      21

<210> SEQ ID NO 48
<211> LENGTH: 20
<212> TYPE: DNA
<213> ORGANISM: Homo sapiens
<220> FEATURE:
<223> OTHER INFORMATION: FGA primer

<400> SEQUENCE: 48
cttctcagat cctctgacac                                        20

<210> SEQ ID NO 49
<211> LENGTH: 25
<212> TYPE: DNA
<213> ORGANISM: Homo sapiens
<220> FEATURE:
<223> OTHER INFORMATION: D1S518 primer

<400> SEQUENCE: 49
gtcaattcct tgttataaaa ttata                                  25

<210> SEQ ID NO 50
<211> LENGTH: 24
<212> TYPE: DNA
<213> ORGANISM: Homo sapiens
<220> FEATURE:
<223> OTHER INFORMATION: D1S518 primer

<400> SEQUENCE: 50
```

```
attggcaact gcattagagt tctc                                          24
```

<210> SEQ ID NO 51
<211> LENGTH: 24
<212> TYPE: DNA
<213> ORGANISM: Homo sapiens
<220> FEATURE:
<223> OTHER INFORMATION: D7S1808 primer

<400> SEQUENCE: 51

```
ggaggaaaag tcttaaacgt gaat                                          24
```

<210> SEQ ID NO 52
<211> LENGTH: 24
<212> TYPE: DNA
<213> ORGANISM: Homo sapiens
<220> FEATURE:
<223> OTHER INFORMATION: D7S1808 primer

<400> SEQUENCE: 52

```
attggccttg atgtgtttgt tact                                          24
```

<210> SEQ ID NO 53
<211> LENGTH: 20
<212> TYPE: DNA
<213> ORGANISM: Homo sapiens
<220> FEATURE:
<223> OTHER INFORMATION: D7S3070 primer

<400> SEQUENCE: 53

```
catttcttct gcccccatga                                               20
```

<210> SEQ ID NO 54
<211> LENGTH: 26
<212> TYPE: DNA
<213> ORGANISM: Homo sapiens
<220> FEATURE:
<223> OTHER INFORMATION: D7S3070 primer

<400> SEQUENCE: 54

```
atttgacagc tgaaaaggtg cagatg                                        26
```

<210> SEQ ID NO 55
<211> LENGTH: 21
<212> TYPE: DNA
<213> ORGANISM: Homo sapiens
<220> FEATURE:
<223> OTHER INFORMATION: D7S3046 primer

<400> SEQUENCE: 55

```
gaggagacag ccagggatat a                                             21
```

<210> SEQ ID NO 56
<211> LENGTH: 27
<212> TYPE: DNA
<213> ORGANISM: Homo sapiens
<220> FEATURE:
<223> OTHER INFORMATION: D7S3046 primer

<400> SEQUENCE: 56

```
atttctctat aacctctctc cctatct                                       27
```

<210> SEQ ID NO 57
<211> LENGTH: 20
<212> TYPE: DNA
<213> ORGANISM: Homo sapiens

```
<220> FEATURE:
<223> OTHER INFORMATION: D10S1426 primer

<400> SEQUENCE: 57
ccccttggtg gtgtcatcct                                                    20

<210> SEQ ID NO 58
<211> LENGTH: 23
<212> TYPE: DNA
<213> ORGANISM: Homo sapiens
<220> FEATURE:
<223> OTHER INFORMATION: D10S1426 primer

<400> SEQUENCE: 58
attgccgatc ctgaagcaat agc                                                23

<210> SEQ ID NO 59
<211> LENGTH: 24
<212> TYPE: DNA
<213> ORGANISM: Homo sapiens
<220> FEATURE:
<223> OTHER INFORMATION: D3S2432 primer

<400> SEQUENCE: 59
attgtttgca tgtgaaacag gtca                                               24

<210> SEQ ID NO 60
<211> LENGTH: 24
<212> TYPE: DNA
<213> ORGANISM: Homo sapiens
<220> FEATURE:
<223> OTHER INFORMATION: BAT-25 primer

<400> SEQUENCE: 60
attctgcatt ttaactatgg ctct                                               24

<210> SEQ ID NO 61
<211> LENGTH: 24
<212> TYPE: DNA
<213> ORGANISM: Homo sapiens
<220> FEATURE:
<223> OTHER INFORMATION: BAT-26 primer

<400> SEQUENCE: 61
tgactacttt tgacttcagc cagt                                               24

<210> SEQ ID NO 62
<211> LENGTH: 24
<212> TYPE: DNA
<213> ORGANISM: Homo sapiens
<220> FEATURE:
<223> OTHER INFORMATION: BAT-26 primer

<400> SEQUENCE: 62
aaccaatcaa cattttaac cctt                                                24
```

DETECTION OF MICROSATELLITE INSTABILITY AND ITS USE IN DIAGNOSIS OF TUMORS

CROSS-REFERENCE TO RELATED APPLICATIONS

This application is a continuation of U.S. patent application Ser. No. 09/663,020, filed Sep. 15, 2000, now U.S. Pat. No. 6,844,152, issued Jan. 18, 2005, which application is incorporated by reference herein in its entirety.

STATEMENT REGARDING FEDERALLY SPONSORED RESEARCH OR DEVELOPMENT

This invention was made using U.S. government Small Business Innovation Research Program Grant CA76834-02 from the National Institutes of Health. The U.S. government retains certain rights to the invention.

TECHNICAL FIELD OF THE INVENTION

This invention relates to the detection of instability in regions of genomic DNA containing simple tandem repeats, such as microsatellite loci. The invention particularly relates to multiplex analysis for the presence or absence of instability in a set of microsatellite loci in genomic DNA from cells, tissue, or bodily fluids originating from a tumor. The invention also relates to the use of microsatellite instability analysis in the detection and diagnosis of cancer and predisposition for cancer.

BACKGROUND OF THE INVENTION

Microsatellite loci of genomic DNA have been analyzed for a wide variety of applications, including, but not limited to, paternity testing, forensics work, and in the detection and diagnosis of cancer. Cancer can be detected or diagnosed based upon the presence of instability at particular microsatellite loci that are unstable in one or more types of tumor cells.

A microsatellite locus is a region of genomic DNA with simple tandem repeats that are repetitive units of one to five base pairs in length. Hundreds of thousands of such microsatellite loci are dispersed throughout the human genome. Microsatellite loci are classified based on the length of the smallest repetitive unit. For example, loci with repetitive units of 1 to 5 base pairs in length are termed "mono-nucleotide", "di-nucleotide", "tri-nucleotide", "tetra-nucleotide", and "penta-nucleotide" repeat loci, respectively.

Each microsatellite locus of normal genomic DNA for most diploid species, such as genomic DNA from mammalian species, consists of two alleles at each locus. The two alleles can be the same or different from one another in length and can vary from one individual to the next. Microsatellite alleles are normally maintained at constant length in a given individual and its descendants; but, instability in the length of microsatellites has been observed in some tumor types (Aaltonen et al., 1993, *Science* 260:812-815; Thibodeau et al., 1993 *Science* 260:816-819; Peltomaki et al., 1993 *Cancer Research* 53:5853-5855; Ionov et al., 1993 *Nature* 363:558-561). This form of genomic instability in tumors, termed microsatellite instability (hereinafter, "MSI"), is a molecular hallmark of the inherited cancer syndrome Hereditary Nonopolyposis Colorectal Cancer (hereinafter, "HNPCC"). The cause of MSI in HNPCC is thought to be a dysfunctional DNA mismatch repair system that fails to reverse errors that occur during DNA replication (Fishel et al., 1993 *Cell* 75:1027-38; Leach et al., 1993 *Cell* 75:215-25; Bronner et al., 1994 *Nature* 368:258-61; Nicolaides et al., 1994 *Nature* 371:75-80; Miyaki et al., 1997 *Nat Genetics* 17:271-2). Insertion or deletion of one or more repetitive units during DNA replication persists without mismatch repair and can be detected as length polymorphisms by comparison of allele sizes found in microsatellite loci amplified from normal and tumor DNA samples (Thibodeau et al, 1993, supra).

MSI has been found in over 90% of HNPCC and in 10-20% of sporadic colorectal tumors (Liu et al., 1996 *Nature Med* 2:169-174; Thibodeau et al., 1993, supra; Ionov et al., 1993 *Nature* 363:558-561; Aaltonen et al., 1993 *Science* 260: 812-816; Lothe et al., 1993 *Cancer Res.* 53: 5849-5852). However, MSI is not limited to colorectal tumors. MSI has also been detected in pancreatic cancer (Han et al., 1993 *Cancer Res* 53:5087-5089) gastric cancer (Id.; Peltomaki et al., 1993 *Cancer Res* 53:5853-5855; Mironov et al., 1994 *Cancer Res* 54:41-44; Rhyu et al., 1994 *Oncogene* 9:29-32; Chong et al., 1994 *Cancer Res* 54:4595-4597), prostate cancer (Gao et al., 1994 *Oncogene* 9:2999-3003), endometrial cancer (Risinger et al., 1993 *Cancer Res* 53:5100-5103; Peltomaki et al., 1993 *Cancer Res* 53:5853-5855), and breast cancer (Patel et al., 1994 *Oncogene* 9:3695-3700).

The genetic basis of HNPCC is thought to be a germ-line mutation in one of several DNA mismatch repair genes (hereinafter "MMR") (Leach et al., 1993 *Cell* 75:1215-1225; Fishel et al., 1993 *Cell* 75:1027-38; Leach et al., 1993 *Cell* 75:215-25; Bronner et al., 1994 *Nature* 368:258-61; Nicolaides et al., 1994 *Nature* 371:75-80; Miyaki et al., 1997 *Nat Genetics* 17:271-2; Papadopoulos et al., 1994 *Science* 263: 1625-1629) Among HNPCC patients, 50-60% have been reported to carry inherited mutations in two mismatch repair genes, MSH2 and MLH1 (Kolodner et al., 1999 *Cancer Research* 59:5068:5074). Moreover, 70-100% of HNPCC cases whose tumors manifest a high frequency MSI (hereinafter "MSI-H") phenotype reportedly have germ-line mutations in these two genes. Few germ-line mutations in MSH6, MSH3, PMS1 and PMS2 genes have been reported in HNPCC patients, indicating that inherited mutations in these mismatch repair genes play a minor role in HNPCC (Peltomaki et al., 1997 *Gastroenterologly* 113:1146-1158; Liu et al., 1996 *Nat Med* 2:169-174; Kolodner et al., 1999 *Cancer Research* 59:5068-5074). Without functional repair proteins, errors that occur during replication are not repaired leading to high mutation rates and increased likelihood of tumor development.

Repetitive DNA is particularly sensitive to errors in replication and therefore dysfunctional mismatch repair systems result in widespread alterations in microsatellite regions. A study of yeast cells without functional mismatch repair systems showed a 2800, 284, 52, and 19 fold increase in mutation rates in mono-, di-, tri-, tetra-, and penta-nucleotide repeats, respectively (Sia et al., 1997 *Molecular and Cellular Biology* 17:2851-2858). Mutations in mismatch repair genes are not thought to play a direct role in tumorigenesis, but rather act by allowing DNA replication errors to persist. Mismatch repair deficient cells have high mutation rates and if these mutations occur in genes involved in tumorigenesis the result can lead to the development of cancer. MSI positive tumors have been found to carry somatic frameshift mutations in mono-nucleotide repeats in the coding region of several genes involved in growth control, apoptosis, and DNA repair (e.g., TGFBRII, BAX, IGFIIR, TCF4, MSH3, MSH6) (Planck et al., 2000

*Genes, Chromosomes & Cancer* 29:33-39; Yamamoto et al., 1998 *Cancer Research* 58:997-1003; Grady et al., 1999 *Cancer Research* 59:320-324; Markowitz et al., 1995 *Science* 268:1336-1338; Parsons et al., 1995 *Cancer Research* 55:5548-5550). The most commonly altered locus is TGF-BRII, in which over 90% of MSI-H colon tumors have been found to contain a mutation in the 10 base polyadenine repeat present in the gene (Markowitz et al., 1995 *Science* 268:1336-1338).

MSI occurs in almost all HNPCC tumors regardless of which mismatch repair gene is involved. MSI has also been shown to occur early in tumorigenesis. These two factors contribute to making MSI analysis an excellent diagnostic test for the detection of HNPCC. In addition, MSI analysis can serve as a useful pre-screening test to identify potential HNPCC patients for further genetic testing. MSI analysis of sporadic colorectal carcinomas is also desirable, since the occurrence of MSI correlates with a better prognosis (Bertario et al., 1999 *International J Cancer* 80:83-7).

One long-standing problem with diagnosing HNPCC is that colon tumor biopsies from a person with HNPCC look the same pathologically as a sporadic colon tumor, making diagnosis of the syndrome difficult. Since prognosis, therapy and follow-up will be different for patients with HNPCC, it is important to find more definitive diagnostic methods. However, mutation detection in HNPCC patients remains difficult because there are at least 5 known MMR genes which are large genes without known hot spots for mutations. Direct gene sequencing remains the most precise method of mutation detection, but is time consuming and expensive (Terdiman et al., 1999 *The American Journal of Gastroenterology* 94:23544-23560). In addition, high sensitivity and specificity can be difficult to obtain with sequencing alone because many mutations that are detected may be harmless polymorphisms that have no affect on the function of the mismatch repair proteins.

DNA analysis of microsatellite loci makes it theoretically possible to develop a blood test for use in the detection of specific types of cancer. Early studies have shown that tumor DNA is released into the circulation, and is present in particularly high concentrations in plasma and serum in a number of different types of cancer (Leon et al., 1977 *Cancer Res* 37:646-650; Stroun et al., 1989 *Oncology* 46:318-322). Since then, DNA released into the blood from several different types of tumors has been detected by analysis of microsatellite DNA using the polymerase chain reaction (hereinafter, "PCR") (Hibi et al., 1998 *Cancer Research* 58:1405-1407; Chen et al., 1999 *Clinical Cancer Research* 5:2297-2303; Kopreski et al., 1999 *Clinical Cancer Research* 5:1961-1965; Fujiwara et al., 1999 *Cancer Research* 59:1567-1571; Chen et al., 1996 *Nature Medicine* 2:1033-1034; Goessl et al., 1998 *Cancer Research* 58:4728-4732; Miozzo et al., 1996 *Cancer Research* 56:2285-2288).

The first tumor-specific gene sequences detected in blood from patients with cancer were mutated K-ras genes (Vasioukhin et al., 1994 *Br. J. Haematol* 86: 774-779; Sorenson et al., 1994 *Cancer Epidemiol. Biomark. Prev.* 3:67-71; Sorenson et al., 2000 *Clinical Cancer Research* 6:2129-2137; Anker et al., 1997 *Gastroenterology* 112:1114-1120). More recently, detection of microsatellite instability in soluble tumor DNA from plasma and serum originating from head and neck squamous cell cancers (Nawroz et al., 1996 *Nature Med* 2:1035-1037) and small cell lung cancers (Chen et al., 1996 *Nature Med* 2:1033-1035) has been shown. These successes have stimulated searches for microsatellite instability in circulating tumor DNA from many other cancer types. Hibi et al., used microsatellite markers to search for the presence of genetic alterations in serum DNA from colon cancer patients (Hibi, K. et al., 1998 *Cancer Research* 58:1405-1407). Hibi et al., also reported that eighty percent of primary tumors in the colon cancer patients displayed MSI and/or loss of heterozygosity (hereinafter, "LOH"), another type of mutation discussed below. No microsatellite or LOH mutations were detected in paired serum DNA. However, identical K-ras mutations were found in corresponding tumor and serum DNAs, indicating that tumor DNA was present in the blood. (Id.)

The detection of circulating tumor cells and micrometastases may also have important prognostic and therapeutic implications. Because disseminated tumor cells are present in very small numbers, they are not easily detected by conventional immunocytological tests, which can only detect a single tumor cell among 10,000 to 100,000 normal cells (Ghoussein et al., 1999 *Clinical Cancer Research* 5:1950-1960). More sensitive molecular techniques based on PCR amplification of tumor-specific abnormalities in DNA or RNA have greatly facilitated detection of occult (hidden) tumor cells. PCR-based tests capable of routinely detecting one tumor cell in one million normal cells have been devised for identification of circulating tumor cells and micrometastases in leukemias, lymphomas, melanoma, neuroblastoma, and various types of carcinomas. (Id.)

Most targets for detection of disseminated tumor cells have been mRNAs. However, some DNA targets have been used successfully, including K-ras mutations in colon cancers, as noted above. The presence of microsatellite instability in some types of tumor cells raises the possibility that these tumor specific mutations created by the instability could serve as a target for PCR-based detection of occult tumor cells.

There has been considerable controversy about how to precisely define and accurately measure MSI (Boland, 1998 *Cancer Research* 58:5248-5257). Reports on the frequency of MSI in various tumors ranges considerably. For example, different studies have reported ranges of 3% to 95% MSI for the frequency of MSI in bladder cancer (Gonzalez-Zulueta et al., 1993 *Cancer Research* 53:28-30; Mao et al., 1996 *PNAS* 91:9871-9875). One problem with defining MSI is that it is both tumor specific and locus dependent (Boland et al. 1998, supra). Thus, the frequency of MSI observed with a particular tumor type in a single study will depend on the number of tumors analyzed, the number of loci investigated, how many loci need to be altered to score a tumor as having MSI and which particular loci were included in the analysis. To help resolve these problems, the National Cancer Institute sponsored a workshop on MSI to review and unify the field (Id.). As a result of the workshop a panel of five microsatellites was recommended as a reference panel for future research in the field. This panel included two mononucleotide loci BAT-25, BAT-26, and three dinucleotide loci D5S346, D2S123, D17S250.

One particular problem in MSI analysis of tumor samples occurs when one of the normal alleles for a given marker is missing due to LOH, and no other novel fragments are present for that marker (Id.). One cannot easily discern whether this represents true LOH or MSI in which the shifted allele has co-migrated with the remaining wild-type allele. In cases like this, the recommendation from the NCI workshop on MSI was not to call it as MSI. One way to minimize this type of problem would be to use loci that displayed low frequency of LOH in colon tumors.

Clinical diagnostic assays used for determining treatment and prognosis of disease require that the tests be highly accurate (low false negatives) and specific (low false positive rate). Many informative microsatellite loci have been identified and recommended for MSI testing (Boland et al. 1998, supra). However, even the most informative microsatellite loci are not 100% sensitive and 100% specific. To compensate for the lack of sensitivity using individual markers, multiple markers can be used to increase the power of detection. The increased effort required to analyze multiple markers can be offset by multiplexing. Multiplexing allows simultaneous amplification and analysis of a set of loci in a single tube and can often reduce the total amount of DNA required for complete analysis. To increase the specificity of an MSI assay for any given type of cancer, it has been recommended that the panel of five highly informative microsatellite loci identified at the National Institute Workshop (see above) be modified to substitute or add other loci of equal utility (Boland et al. 1998, supra, at p. 5250). Increased information yielded from amplifying and analyzing greater numbers of loci results in increased confidence and accuracy in interpreting test results.

Multiplex MSI analysis solves problems of accuracy and discrimination of MSI phenotypes, but the additional complexity can make analysis more challenging. For example, when microsatellite loci are co-amplified and analyzed in a multiplex format, factors affecting ease and accuracy of data interpretation become much more essential. One of the primary factors affecting accurate data interpretation is the amount of stutter that occurs at microsatellite loci during PCR (Bacher & Schumm, 1998 *Profiles in DNA* 2:3-6; Perucho, 1999 *Cancer Research* 59:249-256). Stutter products are minor fragments produced by the PCR process that differ in size from the major allele by multiples of the core repeat unit. The amount of stutter observed in microsatellite loci tends to be inversely correlated with the length of the core repeat unit. Thus, stutter is most severely displayed with mono- and di-nucleotide repeat loci, and to a lesser degree with tri-, tetra-, and penta-nucleotide repeats (Bacher & Schumm, 1998, supra). Use of low stutter loci in multiplexes would greatly reduce this problem. However, careful selection of loci is still necessary in choosing low stutter loci because percent stutter can vary considerably even within a particular repeat type (Micka et al., 1999 *Journal of Forensic Sciences* 44:1-15).

Microsatellite multiplex systems have been primarily developed for use in genotyping, mapping studies and DNA typing applications. These multiplex systems are designed to allow co-amplification of multiple microsatellite loci in a single reaction, followed by detection of the size of the resulting amplified alleles. For DNA typing analysis, the use of multiple microsatellite loci dramatically increases the matching probability over a single locus. Matching probability is a common statistic used in DNA typing that defines the number of individuals you would have to survey before you would find the same DNA pattern as a randomly selected individual. For example, a four locus multiplex system (GenePrint™ CTTv Multiplex System, Promega) has a matching probability of 1 in 252.4 in African-American populations, compared to an eight locus multiplex system (GenePrint™ PowerPlex™ 1.2 System, Promega) which has a matching probability of 1 in $2.74 \times 10^8$ (*Proceedings: American Academy of Forensic Sciences* (Feb. 9-14, 1998), Schumm, James W. et al., p. 53, B88; Id. Gibson, Sandra D. et al., p. 53, B89; Id., Lazaruk, Katherine et al., p. 51, B83; Sparkes, R. et al., 1996 *Int J Legal Med* 109:186-194). Other commercially available multiplex systems for DNA typing include AmpFlSTR Profiler™ and AmpFlSTR COfiler™ (*AmpFlSTR Profiler™ PCR Amplification Kit User's Manual* (1997), i-viii and 1-1 to 1-10; and *AmpFlSTR COfiler™ PCR Amplification Kit User Bulletin* (1998), i-iii and 1-1 to 1-10, both published by Perkin-Elmer Corp). In addition to multiplexes for DNA typing, a few multiplex microsatellite systems have been developed for the detection of diseases, such as cancer. One such system has been developed by Roche Diagnostics, the "HNPCC Microsatellite Instability Test", in which five MSI loci (BAT25, BAT26, D5S436, D17S250, and D2S123) are co-amplified and analyzed. Additional systems are needed, particularly systems that include additional loci displaying high sensitivity to MSI and low stutter for easy and accuracy of analysis.

The materials and methods of the present invention are designed for use in multiplex analysis of particular microsatellite loci of human genomic DNA from various sources, including various types of tissue, cells, and bodily fluids. The present invention represents a significant improvement over existing technology, bringing increased power of discrimination, precision, and throughput to the analysis of MSI loci and to the diagnosis of illness, such as cancer, related to mutations at such loci.

BRIEF SUMMARY OF THE INVENTION

The present invention provides methods and kits for amplifying and analyzing microsatellite loci or sets of microsatellite loci. The present invention also provides methods and kits for detecting cancer in an individual by co-amplifying multiple microsatellite loci of human genomic DNA originating from tumor tissue or cancerous cells.

In one aspect, the present invention provides a method of analyzing micro-satellite loci, comprising: (a) providing primers for co-amplifying in a single tube a set of at least three microsatellite loci of genomic DNA, comprising at least one mono-nucleotide repeat locus and at least two tetra-nucleotide repeat loci; (b) co-amplifying the set of at least three microsatellite loci from a sample of genomic DNA in a multiplex amplification reaction, using the primers, thereby producing amplified DNA fragments; and (c) determining the size of the amplified DNA fragments.

In another aspect, the present invention provides a method of co-amplifying the set of at least three microsatellite loci of at least two different samples of genomic DNA, a first sample originating from normal non-cancerous biological material from an individual and a second sample originating from a second biological material from the individual. The at least two samples of human genomic DNA are co-amplified in separate multiplex amplification reactions, using primers to each of the loci in the set of at least three microsatellite loci. The size of the resulting amplified DNA fragments from the two multiplex reactions are compared to one another to detect instability in any of the at least three microsatellite loci of the second sample of human genomic DNA.

Another embodiment of the present invention is a method of analyzing at least one mono-nucleotide repeat locus of human genomic DNA selected from the group consisting of MONO-11 and MONO-15. The method of analyzing the at least one mono-nucleotide repeat locus selected from the group consisting of MONO-11 and MONO-15 comprises the steps of: (a) providing at least one primer of the at least one mono-nucleotide repeat locus; (b) amplifying the at least one mono-nucleotide repeat locus from a sample of genomic DNA originating from a biological material from an individual human subject, using the at least one primer, thereby producing an amplified DNA fragment; and (c) determining the size of the amplified DNA fragments. The amplified DNA fragments are preferably analyzed to detect microsatellite instability at the at least one mono-nucleotide repeat locus by comparing the size of the amplified DNA fragments to the most commonly observed allele size at that locus in a human population. Alternatively, the method is used to amplify the at least one mono-nucleotide repeat locus of a sample of human genomic DNA from normal non-cancerous biological material from an individual, and microsatellite instability is detected by comparing the resulting amplified DNA fragments to those obtained in step (b).

Another embodiment of the present invention is a kit for the detection of microsatellite instability in DNA isolated from an individual subject, comprising a single container with oligonucleotide primers for co-amplifying a set of at least three microsatellite loci comprising one mono-nucleotide locus and two tetra-nucleotide loci.

The various embodiments of the method and kit of the present invention, described briefly above, are particularly suited for use in the detection of MSI in tumor cells or cancerous cells. Specifically, the method or kit of the present invention can be used to amplify at least one mono-nucleotide repeat locus selected from the group consisting of MONO-11 and MONO-15 or the set of at least three microsatellite loci comprising at least one mononucleotide repeat locus and at least two tetranucleotide repeat loci of at least one sample of genomic DNA from biological material, such as tissue or bodily fluids, preferably biological material containing or suspected of containing DNA from tumors or cancerous cells. For monomorphic or quasi-monomorphic loci, such as MONO-11 and MONO-15, one can compare the resulting pattern to the pattern produced by amplifying normal DNA from any individual in a population with a standard pattern at that locus. However, it is preferable to use DNA from normal tissue of the same individual from whom the tumor DNA was obtained, in order to ensure that a positive result does not reflect a germline mutation, rather than MSI.

The method and kit can also be used to compare the results of multiplex amplification of DNA from normal tissue of an individual to the results of multiplex amplification of DNA from other biological material from the same individual. Use of this particular embodiment of the method of the present invention to detect MSI in tumor cells by comparison to normal cells is illustrated in FIG. 1. Specifically, FIG. 1 shows a tetra-nucleotide repeat (GATA), amplified by a primer pair ("primer A" and "primer B") in a polymerase chain reaction ("PCR"), followed by separation of amplified alleles by size using capillary electrophoresis, and a plot of the fractionated amplified alleles using GeneScan™ software. Note that only the two alleles and small stutter peaks appear in the plot of amplified DNA from normal DNA, while three MSI peaks appear in addition to the two allele peaks in the plot of amplified tumor DNA.

Advantages and a fuller appreciation of the specific attributes of this invention will be gained upon an examination of the following figures, detailed description of preferred embodiments, and appended claims. It is expressly understood that the drawings are for the purposes of illustration and description only, and are not intended as a definition of the limits of the invention.

DETAILED DESCRIPTION OF THE INVENTION

A. Definitions

Figure 1:
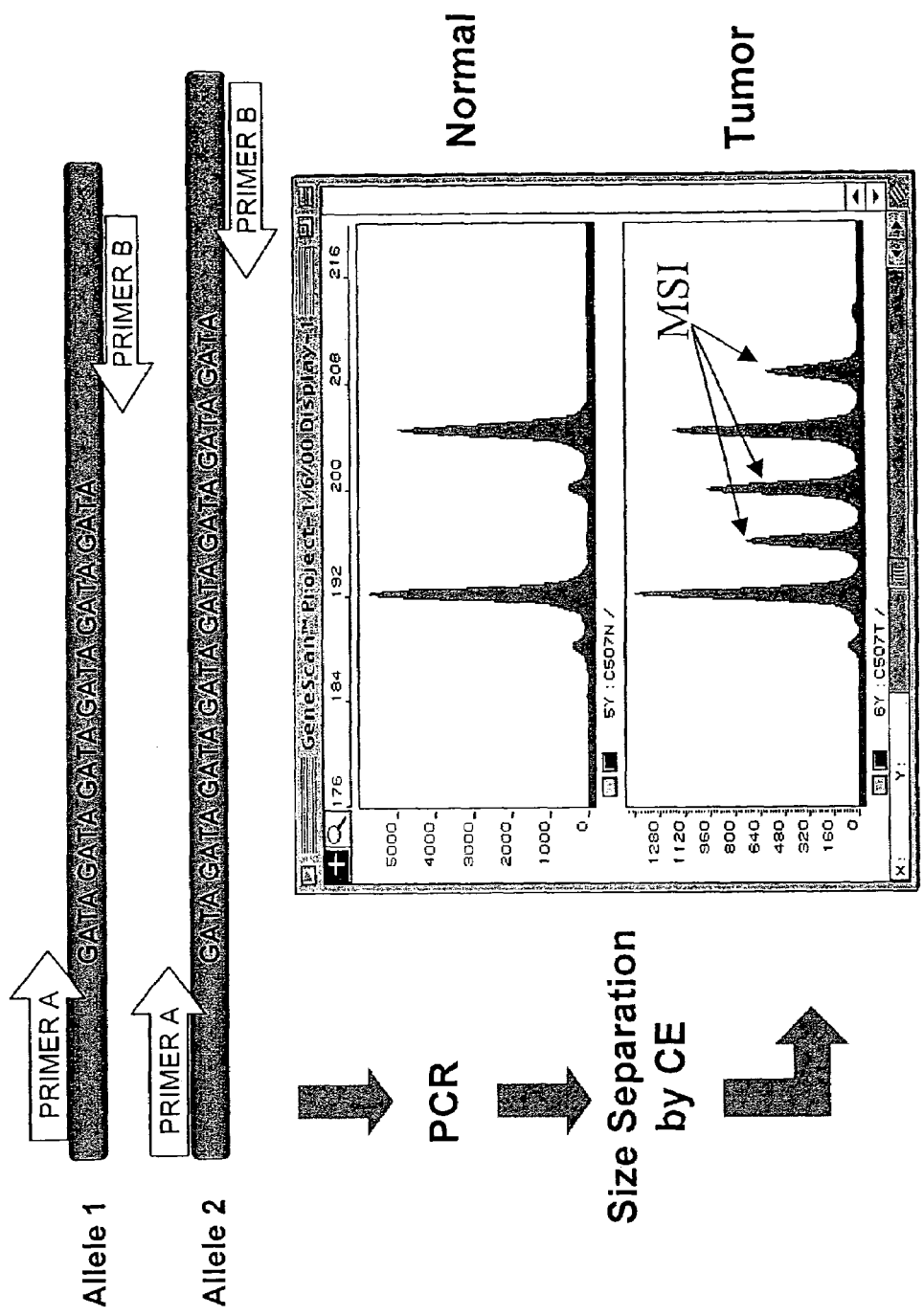
FIG. 1. Illustration of microsatellite instability analysis. The figure is a diagram of a primer pair annealed to a tetra-nucleotide locus on two alleles of the same genomic DNA, and plots of results of capillary electrophoresis of products of amplification of a tetra-nucleotide locus of DNA originating from normal vs. tumor tissue. MSI peaks are indicated in the plot of amplified DNA from tumor tissue.

The following definitions are intended to assist in providing a clear and consistent understanding of the scope and detail of the following terms, as used to describe and define the present invention:

"Allele", as used herein, refers to one of several alternative forms of a gene or DNA sequence at a specific chromosomal location (locus). At each autosomal locus an individual possesses two alleles, one inherited from the father and one from the mother.

"Amplify", as used herein, refers to a process whereby multiple copies are made of one particular locus of a nucleic acid, such as genomic DNA. Amplification can be accomplished using any one of a number of known means, including but not limited to the polymerase chain reaction (PCR) (Saiki, R. K., et al., 1985 Science 230: 1350-1354), transcription based amplification (Kwoh, D. Y., and Kwoh, T. J., American Biotechnology Laboratory, October, 1990) and strand displacement amplification (SDA) (Walker, G. T., et al., 1992 Proc. Natl. Acad. Sci., U.S.A. 89: 392-396).

"Co-amplify", as used herein, refers to a process whereby multiple copies are made of two or more loci in the same container, in a single amplification reaction.

"DNA polymorphism", as used herein, refers to the existence of two or more alleles for a given locus in the population. "Locus" or "genetic locus", as used herein, refers to a unique chromosomal location defining the position of an individual gene or DNA sequence. "Locus-specific primer", as used herein, refers to a primer that specifically hybridizes with a portion of the stated locus or its complementary strand, at least for one allele of the locus, and does not hybridize efficiently with other DNA sequences under the conditions used in the amplification method.

"Loss of Heterozygosity" (hereinafter, "LOH"), as used herein, refers to the loss of alleles on one chromosome detected by assaying for markers for which an individual is constitutionally heterozygous. Specifically, LOH can be observed upon amplification of two different samples of genomic DNA from a particular subject, one sample originating from normal biological material and the other originating from a tumor or pre-cancerous tissues. The tumor exhibits LOH if DNA from the normal biological material produces amplified alleles of two different lengths and the tumor samples produces only one of the two lengths of amplified alleles at the same locus.

"Microsatellite Locus", as used herein, refers to a region of genomic DNA that contains short, repetitive sequence elements of one (1) to seven (7), more preferably one (1) to five (5), most preferably one (1) to four (5) base pairs in length. Each sequence repeated at least once within a microsatellite locus is referred to herein as a "repeat unit." Each microsatellite locus preferably includes at least seven repeat units, more preferably at least ten repeat units, and most preferably at least twenty repeat units.

"Microsatellite Instability" (hereinafter, "MSI"), as used herein, refers to a form of genetic instability in which alleles of genomic DNA obtained from certain tissue, cells, or bodily fluids of a given subject change in length at a microsatellite locus. Specifically, MSI can be observed upon amplification of two different samples of genomic DNA from a particular subject, such as DNA from healthy and cancerous tissue, wherein the normal sample produces amplified alleles of one or two different lengths and the tumor sample produces amplified alleles wherein at least one of the alleles is of a different length from the amplified alleles of the normal sample of DNA at that locus. MSI generally appears as a result of the insertion or deletion of at least one repeat unit at a microsatellite locus.

"MSI-H", as used herein, is a term used to classify tumors as having a high frequency of MSI. When five microsatellite loci are analyzed, such as the five microsatellite loci of selected by a workshop on HNPCC at the National Cancer Institute in 1998 for use in the detection of HNPCC, a tumor is classified as MSI-H when at least two of the loci show instability (Boland, 1998 Cancer Research 58: 5248-5257). When more than five microsatellite loci are analyzed, a tumor is classified as MSI-H when at least 30% of the microsatellite loci of genomic DNA originating from the tumor is are found to be unstable.

"MSI-L", as used herein, is a term used to classify tumors as having a low frequency of MSI. When five microsatellite loci are analyzed, such as the five microsatellite loci of selected by a workshop on HNPCC at the National Cancer Institute in 1998 for use in the detection of HNPCC, a tumor is classified as MSI-L when only one of the loci shows instability. When more than five microsatellite loci are analyzed, a tumor is classified as MSI-L when less than 30% of the microsatellite loci of genomic DNA originating from the tumor is are found to be unstable. MSI-L tumors are thought to represent a distinct mutator phenotype with potentially different molecular etiology than MSI-H tumors (Thibodeau, 1998; Wu et al., 1999, Am J Hum Genetics 65:1291-1298). To accurately distinguish MSI-H and MSI-L phenotypes it has been recommended that more than five microsatellite markers be analyzed (Boland, 1998, supra; Frazer et al., 1999 Oncology Research 6:497-505).

"MSS", as used herein, refers to tumors which are microsatellite stable, when no microsatellite loci exhibit instability. The distinction between MSI-L and MSS can also only be accomplished when a significantly greater number of markers than five are utilized. The National Cancer Institute recommended use of an additional 19 mono- and di-nucleotide repeat loci for this purpose, and for the purpose of making clearer distinctions between MSI-H and MSI-L tumors, as described above (Boland, 1998, supra).

"MSI-L/S", as used herein, refers to all classified as either MSI-L or MSS.

"Microsatellite marker", as used herein, refers to a fragment of genomic DNA which includes a microsatellite repeat and nucleic acid sequences flanking the repeat region.

"Monomorphic", as used herein, refers to a locus of genomic DNA where only one allele pattern has been found to be present in the normal genomic DNA of all members of a population.

"Nucleotide", as used herein, refers to a basic unit of a DNA molecule, which includes one unit of a phosphatidyl back bone and one of four bases, adenine ("A"); thymine ("T"); guanine ("G"); and cytosine ("C").

"Polymerase chain reaction" or "PCR", as used herein, refers to a technique in which cycles of denaturation, annealing with primer, and extension with DNA polymerase are used to amplify the number of copies of a target DNA sequence by approximately $10^6$ times or more. The polymerase chain reaction process for amplifying nucleic acid is covered by U.S. Pat. Nos. 4,683,195 and 4,683,202, which are incorporated herein by reference for a description of the process.

"Primer", as used herein, refers to a single-stranded oligonucleotide or DNA fragment which hybridizes with a strand of a locus of target DNA in such a manner that the 3' terminus of the primer may act as a site of polymerization using a DNA polymerase enzyme.

"Primer pair", as used herein, refers to a pair of primers which hybridize to opposite strands a target DNA molecule, to regions of the target DNA which flank a nucleotide sequence to be amplified.

"Primer site", as used herein, refers to the area of the target DNA to which a primer hybridizes.

"Quasi-monomorphic", as used herein, refers to a locus of genomic DNA where only one allele pattern has been found to be present in the normal genomic DNA of almost all the members of a population.

"Stutter", as used herein, refers to a minor fragment observed after amplification of a microsatellite locus, one or more repeat unit lengths smaller than the predominant fragment or allele. It is believed to result from a DNA polymerase slippage event during the amplification process (Levinson & Gutman, 1987 Molecular Bioliolgy Evolution 4:203; Schlotterer and Tautz, 1992 Nucleic Acids Research 20:211).

B. Selection of Loci to be Amplified or Co-Amplified:

At least one MSI locus amplified or co-amplified in each of the embodiments of the present invention illustrated and discussed herein is a mono-nucleotide repeat locus. Such loci have been shown to very susceptible to alteration in tumors with dysfunctional DNA mismatch repair systems (Parsons., 1995 supra), making such loci particularly useful for the detection of cancer and other diseases associated with dysfunctional DNA mismatch repair systems. One group of researchers reported that by amplifying and analyzing a single mono-nucleotide repeat locus, BAT-26, they were able to correctly confirm the MSI-H status of 159 out of 160 (99.4% accuracy) tumor samples (Hoang et al., 1997 Cancer Research 57:300-303).

Some mono-nucleotide repeat loci, including BAT-26, have also been identified as having quasi-monomorphic properties. Monomorphic or quasi-monomorphic properties make the comparison of normal/tumor pairs simpler, since PCR products from normal samples are generally all the same size and any alterations in tumor samples are easily identified.

Figure 2:
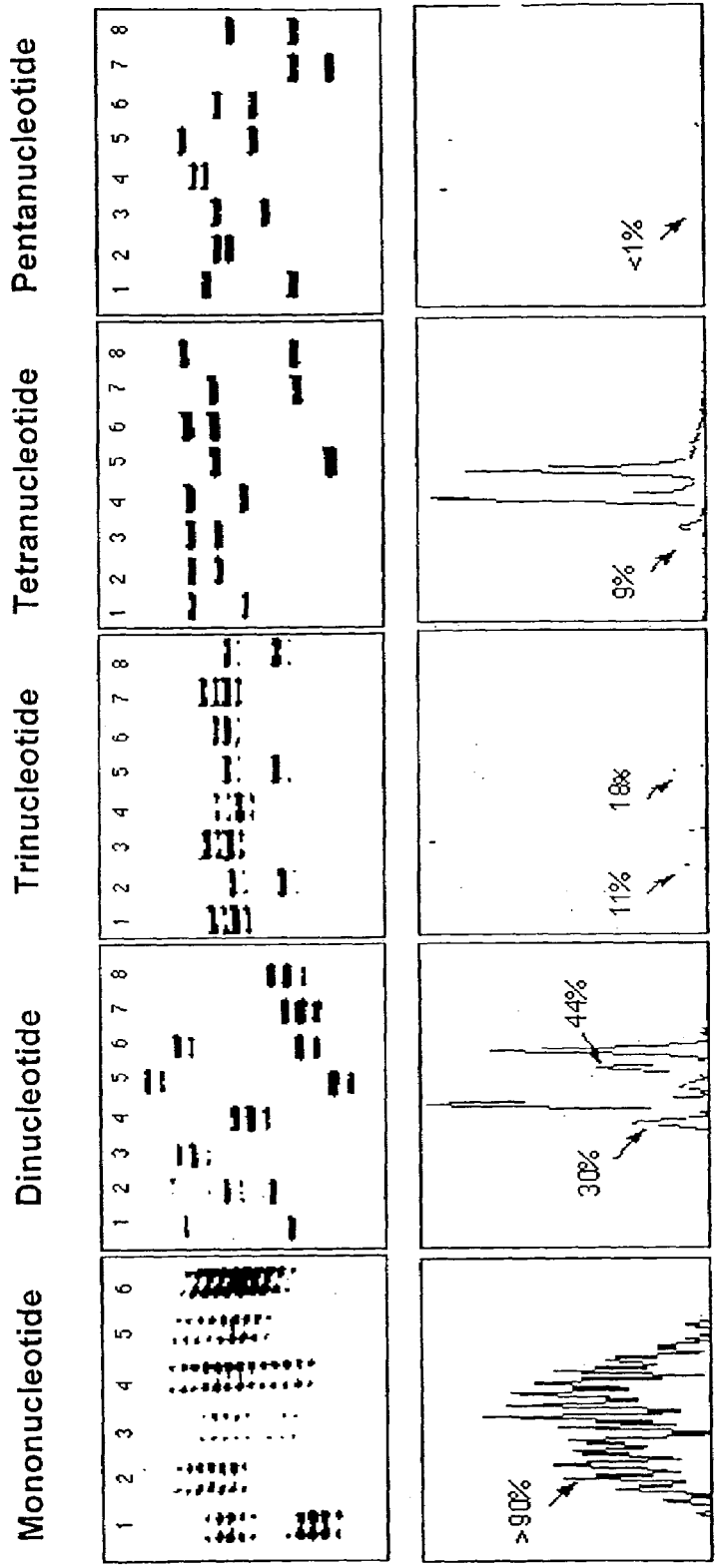
FIG. 2. Illustration of effect of microsatellite repeat unit length on amount of stutter observed. The figure includes a diagram of a primer pair annealed to a tetranucleotide repeat locus on two different alleles of genomic DNA, and a set of fluorescent scans and plots of amplified mono-, di-, tri-, tetra-, and penta-nucleotide repeat loci from human genomic DNA from various individuals, amplified and fractionated by gel or by capillary electrophoresis.

The principal draw-back to using a mono-nucleotide repeat locus in the analysis of genomic DNA is that amplification of any such locus results in a large number of extraneous amplified fragments of DNA of various lengths, the product of "stutter" during the amplification reaction. Such artifacts are present to a lesser degree in the products of amplifying loci with increasingly longer repeat units. For an illustration of the relationship between repeat unit length and the presence of extraneous amplified fragments, see FIG. 2. FIG. 2 shows increased stutter artifacts with decreasing repeat unit length from penta-nucleotide to mono-nucleotide repeat loci.

When a mono-nucleotide locus is monomorphic or quasi-monomorphic, however, one can readily detect shifts in the size of an allele, indicating MSI, even in the presence of a high degree of stutter. When a locus is quasi-monomorphic, detection of shifts in size can be done by comparison of amplified alleles from genomic DNA from biological material of an individual, such as tumor tissue or bodily fluids, suspected of exhibiting microsatellite instability to the most commonly observed allele size at that locus in a population. This feature enables one to use a single standard or panel of standard allele patterns to analyze individual results, minimizing the amount of samples which must be taken from an individual in order to detect microsatellite instability in certain genomic DNA of the individual.

At least one of the microsatellite loci amplified in the method or using the kit of the present invention is preferably a mono-nucleotide repeat locus, more preferably a quasi-monomorphic mono-nucleotide repeat locus. The mono-nucleotide repeat locus selected for use in the methods and kits of the present invention is preferably unstable in cancerous biological material, but not in normal biological material. BAT-25 and BAT-26 have been identified as mono-nucleotide repeat loci useful in the identification of MSI in colorectal tumors characteristic of Hereditary Nonpolyposis Colon Cancer (Zhou et al., 1998 Genes, Chromosomes & Cancer 21:101-107; Dietmaier et al., 1997 Cancer Research 57:4749-4756; Hoang et al., 1997 Cancer Research 57:300-303). Two additional loci, identified herein as MONO-11 and MONO-15 were identified through a search of a public computerized database of sequence information (GenBank), and found to have the preferred characteristics for such loci, identified above. The search for and identification of mono-nucleotide repeat loci suitable for use in the present invention is illustrated in Example 2. Similar techniques could be used to identify other mono-nucleotide repeat loci suitable for use in the methods and kits of the present invention.

The mono-nucleotide repeat loci amplified or co-amplified according to the present methods or using the present kits are preferably quasi-monomorphic and exhibit instability in the type of tissue of interest for a given application. MONO-11 and MONO-15, have been be particularly useful in the methods and kits of the present invention. Both loci are quasi-monomorphic and exhibit instability in several cancerous tumor tissues. At least one, more preferably at least two mono-nucleotide repeat microsatellite loci are amplified or co-amplified in the method of the present invention.

At least one mono-nucleotide repeat locus and at least two tetra-nucleotide repeat loci are co-amplified and analyzed according to at least some embodiments of the method and kits of the present invention. Tetra-nucleotide repeat loci inherently generate very few stutter artifacts when amplified, compared to microsatellite loci with shorter repeat units, particularly compared to mono- and di-nucleotide repeat loci. (See, e.g., FIG. 2.) Such artifacts can be difficult to distinguish from MSI if a shifted allele occurs at the stutter position of the second allele. Therefore, concerns about interpretation, and the need for quasi-monomorphism in order to make data interpretation possible is not present, as it is for mono-nucleotide repeat loci. In fact, one can even use tetra-nucleotide repeat loci which are highly polymorphic in a population, provided it is stable within an individual subject. Such loci are commonly used in DNA typing.

As with any locus to be amplified in any method or using any kit of the present invention, the tetra-nucleotide repeat loci are preferably selected on the basis of being stable in the DNA of an individual except in the type of biological material of interest. Preferred tetra-nucleotide repeat loci used in the methods and kits of the present invention include: FGA, D1S518, D1S547, D1S1677, D2S1790, D3S2432, D5S818, D5S2849, D6S1053, D7S3046, D7S1808, D7S3070, D8S1179, D9S2169, D10S1426, D10S2470, D12S391, D17S1294, D17S1299, and D18S51.

Additional mono-nucleotide or tetra-nucleotide loci with the same preferred criteria described above are preferably co-amplified with the set of at least three microsatellite loci described above. However, it is contemplated that microsatellite loci other than mono-nucleotide repeat or tetra-nucleotide repeat loci could be included in the set of at least three microsatellite loci co-amplified and analyzed according to the method or using the kit of the present invention.

Preferred methods for selection of loci and sets of loci amplified and analyzed according to the methods or using the kits of the present invention are discussed further, herein below. However, once the method and materials of this invention are disclosed, additional methods of selecting loci, primer pairs, and amplification techniques for use in the method and kit of this invention are likely to be suggested to one skilled in the art. All such methods are intended to be within the scope of the appended claims.

C. Additional Screening of Loci

When the method or kit of the present invention is to be used in clinical diagnostic assays to be used to determine treatment and prognosis of disease, it must be designed to produce results which are highly accurate (low false negatives) and specific (low false positive rate). Informative microsatellite loci are preferably identified by screening, more preferably by very extensive screening (see Examples 1 and 2). However, even the most informative microsatellite loci are not 100% sensitive and 100% specific.

The power of individual markers at detecting the presence of MSI in tissue associated with a particular disease, such as cancerous tumors, can be increased tremendously by multiplexing multiple markers. Increased information yielded from amplifying and analyzing greater numbers of loci results in increased confidence and accuracy in interpreting test results. To obtain needed sensitivity in detecting or diagnosing diseases such as cancer, it has been recommended that one analyze five or more highly informative microsatellite loci (Boland, 1998 *Cancer Research* 58: 5248-5257). Multiplexing of microsatellite loci further simplifies MSI analysis by allowing simultaneous amplification and analysis of all multiple loci, while reducing the amount of often-limited DNA required for amplification.

Another common problem in MSI determination relates to the occurrence of an intermediate MSI phenotype where only a small percentage (<30%) of microsatellite markers are altered in tumors (Boland, 1998, supra). These MSI-low tumors are thought to represent a distinct mutator phenotype with potentially different molecular etiology than MSI-H tumors (Thibodeau et al., 1993 *Science* 260: 816-8; Wu et al., 1999 *Am J Hum Genetics* 65:1291-1298; Kolodner et al., 1999 *Cancer Research* 59:5068-5074; Wijnen et al., 1999 *Nature Genetics* 23:142-144). It is not clear however if there is a real difference between MSI-L and MSS tumors. For purposes of diagnosis, MSI-L and MSS tumors are generally considered as one stable phenotypic class. To accurately distinguish MSI-H and MSI-L phenotypes it has been recommended that multiple microsatellite markers be analyzed (Boland, 1998; Frazer, 1999 supra).

Figure 4:
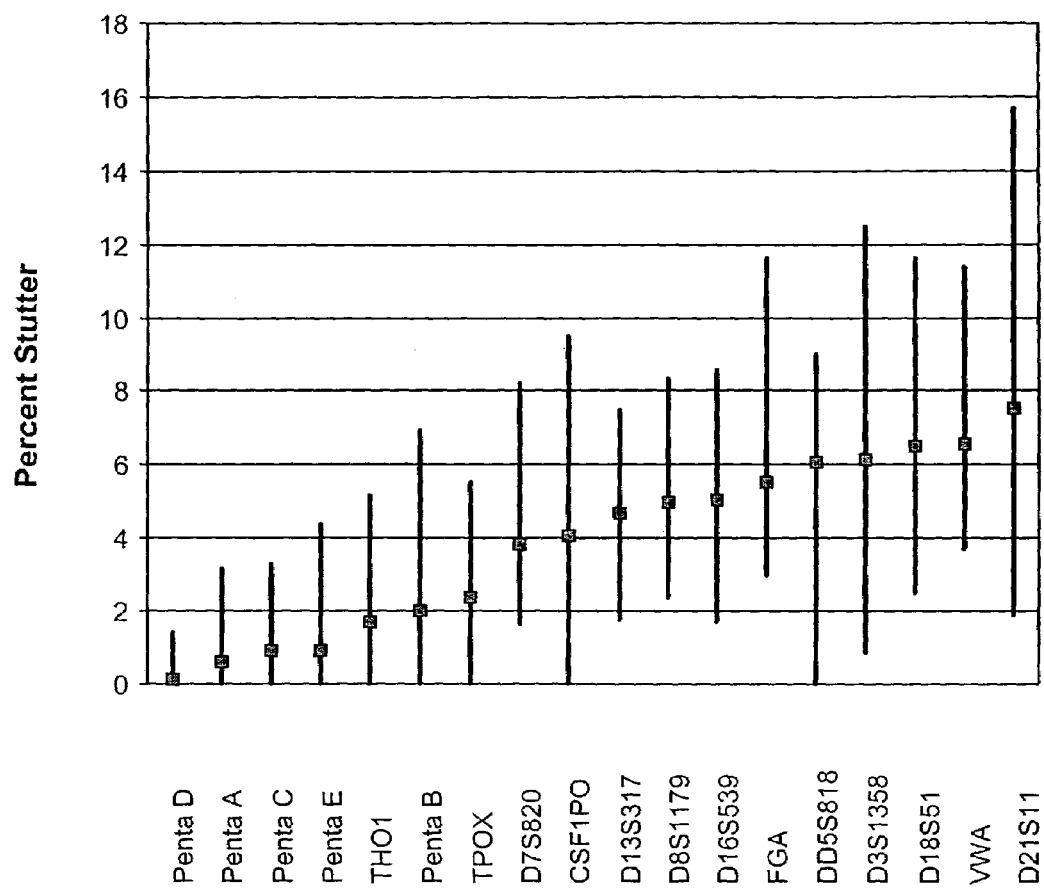
FIG. 4. Illustration of variance in amount of stutter within selected tetranucleotide and pentanucleotide repeat loci. The figure is a plot of the variability in percent stutter observed in a 13 different tetra-nucleotide and 5 different pentanucleotide repeat loci. The boxes represent the average percent stutter and the solid bars the range of stutter observed for each locus.

It is contemplated that when the loci are to be co-amplified and analyzed in a multiplex amplification reaction, additional factors are taken into account, including ease and accuracy of interpretation of data. One of the primary factors affecting accurate data interpretation is the amount of stutter that occurs at microsatellite loci during PCR. Tetra-nucleotide repeat loci were chosen for inclusion in the MSI multiplex analyzed according to the method and using the kit of the present invention because they display considerably less stutter that shorter repeat types like di-nucleotides (FIG. 2). However, careful selection of loci is still necessary in choosing low stutter loci because % stutter can vary considerably even within a particular repeat type (FIG. 4). Mono-nucleotide repeat loci were chosen for individual analysis and for inclusion in the MSI Multiplex because of high rates of instability in diseased biological material of interest.

Incidence of LOH is another factor in the selection of MSI loci to be amplified and analyzed in the methods or kits of the present invention. LOH can result in misidentification of a missing normal allele at a microsatellite marker as an indication of MSI when no other novel fragments are present for that marker. Specifically, one cannot easily discern whether this represents true LOH or MSI in which the shifted allele has co-migrated with the remaining wild-type allele. In order to minimize the problem described above, the microsatellite markers selected for use in the present methods and kits preferably exhibit a low frequency of LOH, preferably no more than about 20% LOH, more preferably no more than about 14% LOH, even more preferably, no more than about 3% LOH.

It is a relatively uncommon occurrence for a microsatellite market to possess all necessary attribute described above (i.e., high sensitivity, high specificity, low stutter, low LOH). The threshold for an MSI analysis system to be used in a diagnostic test is even higher, requiring robust and reproducible results from multiple loci in one assay using small quantities of DNA from difficult samples and be able to distinguish between MSI-L and MSI-H phenotypes. All the specific preferred mono- and tetra-nucleotide repeat loci identified herein above as being preferred for use in the present invention were found to meet each of the criteria for MSI loci suitable for use in diagnostic analysis, set forth herein above.

Additional loci selection criteria particular to the two principal types of MSI loci amplified in the preferred multiplex analysis methods and using the kits of the present loci are described below.

D. Design of Primers

Primers for one or more microsatellite loci are provided in each embodiment of the method and kit of the present invention. At least one primer is provided for each locus, more preferably at least two primers for each locus, with at least two primers being in the form of a primer pair which flanks the locus. When the primers are to be used in a multiplex amplification reaction it is preferable to select primers and amplification conditions which generate amplified alleles from multiple co-amplified loci which do not overlap in size or, if they do overlap in size, are labeled in a way which enables one to differentiate between the overlapping alleles.

Primers suitable for the amplification of individual loci preferably co-amplified according to the methods of the present invention are provided in Example 4, Table 9, herein below. Primers suitable for use in a preferred multiplex of nine loci (i.e., BAT-25, D10S1426, D3S2432, BAT-26, D7S3046, D7S3070, MONO-15, D1S518, and D7S1808) are described in Example 6, Table 11. Guidance for designing this and other multiplexes is provided, below. It is contemplated that other primers suitable for amplifying the same loci or other sets of loci falling within the scope of the present invention could be determined by one of ordinary skill in the art.

E. Design and Testing of MSI Multiplex

The method of multiplex analysis of microsatellite loci of the present invention contemplates selecting an appropriate set of loci, primers, and amplification protocols to generate amplified alleles from multiple co-amplified loci which preferably do not overlap in size or, more preferably, which are labeled in a way which enables one to differentiate between the alleles from different loci which overlap in size. Combinations of loci may be rejected for either of the above two reasons, or because, in combination, one or more of the loci do not produce adequate product yield, or fragments which do not represent authentic alleles are produced in this reaction.

The following factors are preferably taken into consideration in deciding upon which loci to include in a multiplex of the present invention. To effectively design the microsatellite multiplex, size ranges for alleles at each locus are determined. This information is used to facilitate separation of alleles between all the different loci, since any overlap could result in an allele from one locus being inappropriately identified as instability at another locus.

Figure 3:
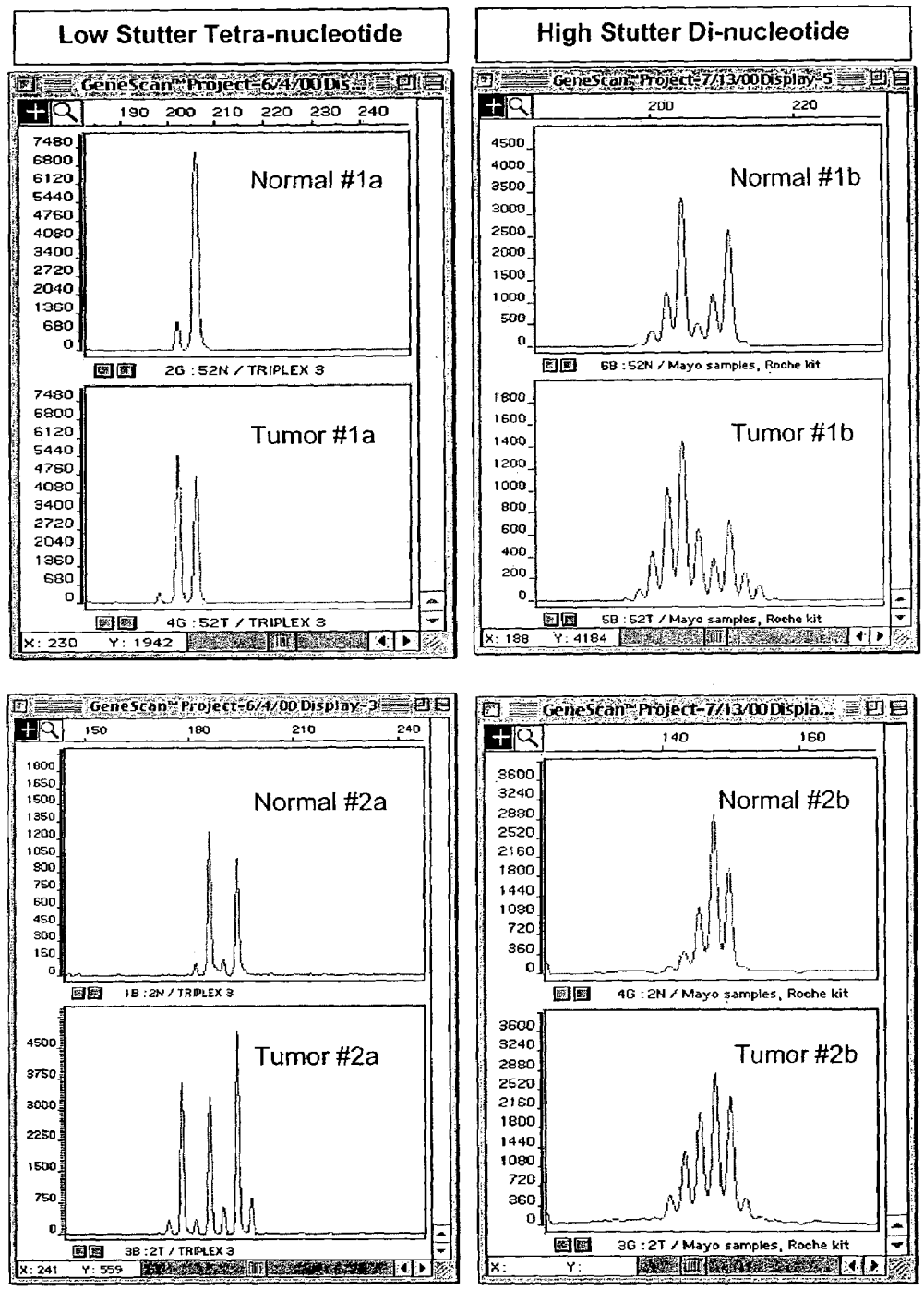
FIG. 3. Demonstration that low stutter tetranucelotide repeat loci are easier to interpret than high stutter dinucleotide repeat loci. The figure is a plot of results of capillary electrophoresis of products of the amplification of two tetra-nucleotide and two di-nucleotide repeat loci of two different sets of samples of DNA originating from normal vs. tumor tissue.

The amount of stutter exhibited by non-mononucleotide repeat loci is also preferably taken into consideration; as the amount of stutter exhibited by a locus can be a major factor in the ease and accuracy of interpretation of data. It is preferable to conduct a population study to determine the level of stutter present for each non-mono-nucleotide repeat locus. As noted above, tetra-nucleotide repeat markers display considerably less stutter that shorter repeat types like di-nucleotides and therefore can be accurately scored in MSI assays (FIGS. 2 and 3)(Bacher & Schumm, 1998 *Profiles in DNA* 2(2):3-6). Note that even within a class of microsatellite loci, such as tetra- and penta-nucleotide repeat loci, known to exhibit low stutter, the percent stutter can vary considerably within the repeat type (FIG. 3; see also FIG. 2) (Micka et al., 1999, supra).

Although at least one mono-nucleotide and at least two tetra-nucleotide repeat loci are included in the multiplex of MSI loci co-amplified according to the method or using the kit of the present invention, additional mono-nucleotide and/or tetra-nucleotide repeat loci can be included in the multiplex. It is also contemplated that multisatellite loci other than mono- or tetra-nucleotide repeat loci meeting the same or similar criteria to the criteria described above would be included in the multiplex.

The multiplex analyzed according to the present invention preferably includes a set of at least three MSI loci. It more preferably includes a set of at least five MSI loci, even more preferably a set of at least nine MSI loci. When the multiplex is a set of at least nine loci, it is most preferably a set of the following loci: BAT-25, D10S1426, D3S2432, BAT-26, D7S3046, D7S3070, MONO-15, D1S518, and D7S1808. A list of primers suitable for use in this multiplex is provided in Table 11 of Example 6 below.

It is also contemplated that other factors, such as successful combinations of materials and methods, are taken into consideration in designing a multiplex of MSI loci. Determination of such additional factors can be determined by following the selection methods and guidelines disclosed herein, and by using techniques known to one of ordinary skill in the art of the present invention. Specifically, the same or substantially similar techniques can be used to identify the preferred MSI loci and sets of MSI loci described herein below to select primer pair sequences, and to adjust primer concentrations to identify an equilibrium in which all included loci may be amplified. In other words, once the method and materials of this invention are disclosed, various methods of selecting loci, primer pairs, and amplification techniques for use in the method and kit of this invention are likely to be suggested to one skilled in the art. All such methods are intended to be within the scope of the present claims.

F. Sources of Genomic DNA

The genomic DNA amplified or co-amplified according to the methods of the present invention originates from biological material from an individual subject, preferably a mammal, more preferably from a dog, cat, horse, sheep, mouse, rat, rabbit, monkey, or human, even more preferably from a human or a mouse, and most preferably from a human being. The biological material can be any tissue, cells, or biological fluid from the subject which contains genomic DNA. The biological material is preferably selected from the group consisting of tumor tissue, disseminated cells, feces, blood cells, blood plasma, serum, lymph nodes, urine, and other bodily fluids.

The biological material can be in the form of tissue samples fixed in formalin and embedded in paraffin (hereinafter "PET"). Tissue samples from biopsies are commonly stored in PET for long term preservation. Formalin creates cross-linkages within the tissue sample which can be difficult to break, sometimes resulting in low DNA yields. Another problem associated with formalin-fixed paraffin-embedded samples is amplification of longer fragments is often problematic. When DNA from such samples is used in multiplex amplification reactions, a significant decrease in peak heights is seen with increasing fragment size. The microsatellite analysis method and kit of the present invention are preferably designed to amplify and analyze DNA from PET tissue samples. (See Example 7 for an illustration of amplification of such samples using a method of the present invention.) When the method or kit of the present invention is used in the analysis or detection of tumors, at least one sample of genomic DNA analyzed originates from a tumor. When a monomorphic or quasi-monomorphic locus, such as MONO-11 or MONO-15 is amplified, the size of the resulting amplified alleles can be compared to the most commonly observed allele size at that locus in the general population. The present method and kit is preferably used to diagnose or detect tumors by co-amplifying at least two different samples of DNA from the same individual, wherein one of the two samples originates from normal non-cancerous biological material.

The present invention is further explained by the following examples which should not be construed by way of limiting the scope of the present invention.

EXAMPLE 1

Screening Microsatellite Markers for Frequency of MSI

In this example, microsatellite markers in DNA isolated from tumors were compared to microsatellite markers in DNA isolated from normal tissue or cells in order to detect MSI. Specifically, microsatellite loci were amplified from paired normal/tumor DNA samples and genotyped. If one or more different alleles were present in the tumor DNA sample that were not found in normal sample from the same individual, then it was scored as MSI positive. Di-nucleotide, tetra-nucleotide and penta-nucleotide repeat microsatellite markers were analyzed for frequency of alteration to determine the relative sensitivity of particular markers to MSI. Detailed information about the specific procedures used in this example are provided herein, below.

Tissues and DNA isolation. Matched normal (blood) and neoplastic tissue samples for 39 patients were obtained from the Cooperative Human Tissue Network (hereinafter, "CHTN")(Ohio State University, Columbus, Ohio). After surgical resection, tissue samples were frozen in liquid nitrogen and stored at −70° C. Blood samples were collected by venipuncture using vacuum tubes. DNA extraction from blood and solid tissues was performed either by standard Phenol/chloroform method (Sambrook et al., 1989 *Molecular Cloning: A Laboratory Manual*, Cold Springs Harbor Press, Cold Springs Harbor, N.Y.) or with QIAamp Blood and Tissue Kit (QIAGEN, Santa Clarita, Calif.) following manufactures protocol.

PCR and Microsatellite Analysis. Fluorescently labeled primers from 275 microsatellite loci were used to amplify template DNA from normal/tumor pairs of samples. Two hundred and forty-five tetra-nucleotide repeat markers from the Research Genetics CHLC/Weber Human Screening Set Version 9.0 were evaluated (Research Genetics, Huntsville, Ala.). Additional primer sets for tetra-nucleotide and penta-nucleotide repeat markers were obtained from Promega Corporation (Madison, Wis.) (PowerPlex™ 16 System contains D3S1358, TH01, D21S11, D18S51; Penta E, D5S818; D13S317, D7S820, D16S539, CSF1PO, Penta D, vWA, D8S1179, TPOX, and FGA loci). Penta-nucleotide repeat markers TP53, Penta A, Penta B, Penta C, Penta D, Penta E, Penta F and Penta G or were custom synthesized (Promega Corporation, Madison, Wis.) using sequence data from public databases Di-nucleotide markers included for comparison purposes (D8S254, NM23, D18S35, D5S346, TP53-di, D2S123, D1S2883, D3S1611, D7S501) were obtained from PE Biosystems (now doing business as Applied Biosystems Group, Foster City, Calif.).

Markers from Research Genetics, Human Screening Set Version 9.0, were multiplexed and screened for MSI using 2.5 ng of DNA in 10 µl PCR reactions described below. Other loci were evaluated as monoplexes using 1 ng DNA in 25 µl PCR reactions as described below. All markers were PCR amplified under the same conditions in using a Perkin-Elmer® GeneAmp PCR System 9600 Thermal Cycler, except as indicated otherwise below. Microsattelite markers from the PowerPlex™ 16 System (Technical Manual #TMD012, Promega Corporation, Madison, Wis.) and dinucleotide repeat markers from the Microsatellite RER Assay system (see product literature from PE Biosystems, non Applied Biosystems, Foster City, Calif.) were analyzed following manufacture's protocol.

TABLE 1

10 µl triplex PCR reaction for Research Genetics markers

| PCR Master Mix Component | Volume Per Sample |
|---|---|
| Nuclease Free Water | 3.30 µl |
| 10X GoldST★R Buffer (Promega) | 1.00 µl |
| Primer 1 | 0.50 µl |
| Primer 2 | 0.50 µl |
| Primer 3 | 0.50 µl |
| Primer 4 | 0.50 µl |
| Primer 5 | 0.50 µl |

TABLE 1-continued

10 µl triplex PCR reaction for Research Genetics markers

| PCR Master Mix Component | Volume Per Sample |
|---|---|
| Primer 6 | 0.50 µl |
| AmpliTaq Gold DNA Polymerase (5 Units/µl) (Perkin Elmer) | 0.15 µl |
| DNA (1 ng/µl) | 2.50 µl |
| Total Reaction Volume | 10.00 µl |

TABLE 2

25 µl PCR reaction

| PCR Master Mix Component | Volume Per Sample |
|---|---|
| Nuclease Free Water | 17.45 µl |
| GoldST★R 10X Buffer (Promega) | 2.50 µl |
| 10X Primer Pair Mix (10 µM) | 2.50 µl |
| AmpliTaq Gold DNA Polymerase (5 Units/µl) (Perkin Elmer) | 0.05 µl |
| Template DNA (0.4 ng/µl) | 2.50 µl |
| Total Reaction Volume | 25.00 µl |

TABLE 3

Cycling profile for PE 9600 Thermal Cycler

| 1 cycle | 95° C. for 11 minutes |
|---|---|
| 1 cycle | 96° C. for 1 minute |
| 10 cycles | 94° C. for 30 seconds |
|  | ramp 68 seconds to 56° C., hold for 30 seconds |
|  | ramp 50 seconds to 70° C., hold for 45 seconds |
| 20 cycles | 94° C. for 30 seconds |
|  | ramp 60 seconds to 56° C., hold for 30 seconds |
|  | ramp 50 seconds to 70° C., hold for 45 seconds |
| 1 cycle | 60° C. for 30 minutes |
| 1 cycle | Soak 4° C. |

One microliter of PCR product (Research Genetics markers were first diluted 1:4 in 1× GoldST★R PCR buffer) was combined with 1 µl of Internal Lane Standard (Promega Corporation, Madison, Wis.) and 24 µl deionized formamide. Samples were denatured by heating at 95° C. for 3 minutes and immediately chilled on ice for 3 minutes. Separation and detection of amplified fragments was performed on an ABI PRISM® 310 Genetic Analyzer following the standard protocol recommended in the User's Manual with the following settings: 5 second Injection Time, 15 kV Injection Voltage, 15 kV Run Voltage, 60° C. Run Temperature, and 28 minute Run Time.

Assay Interpretation. Identification of normal and tumor allele sizes was accomplished by examining the appropriate electropherogram from the ABI PRISM 310 Genetic Analyzer (Applied Biosystems) and determining the predominate peaks for each locus. One or two peaks or alleles can be present for each locus in normal samples depending upon whether individual is homozygous or heterozygous for a particular marker. Allelic patterns or genotypes for normal and tumor pairs were compared and scored as MSI positive if one or more different alleles were present in the tumor DNA samples that were not found in normal sample from the same individual.

A wide range in frequency of alteration was observed in between samples and between markers evaluated. Samples were divided into two groups based on the frequency of alteration using guidelines recommended in NCI Workshop on MSI (Boland et al., 1998). Samples with greater that 30-40% of markers exhibiting alteration in tumor samples were classified as MSI-H and <30-40% as MSI-L. Samples with no alterations were classified as microsatellite stable (MSS). Based on this definition of MSI phenotypes, nine samples were classified as MSI-H and the remaining 30 as either MSI-L or MSS.

Figure 5:
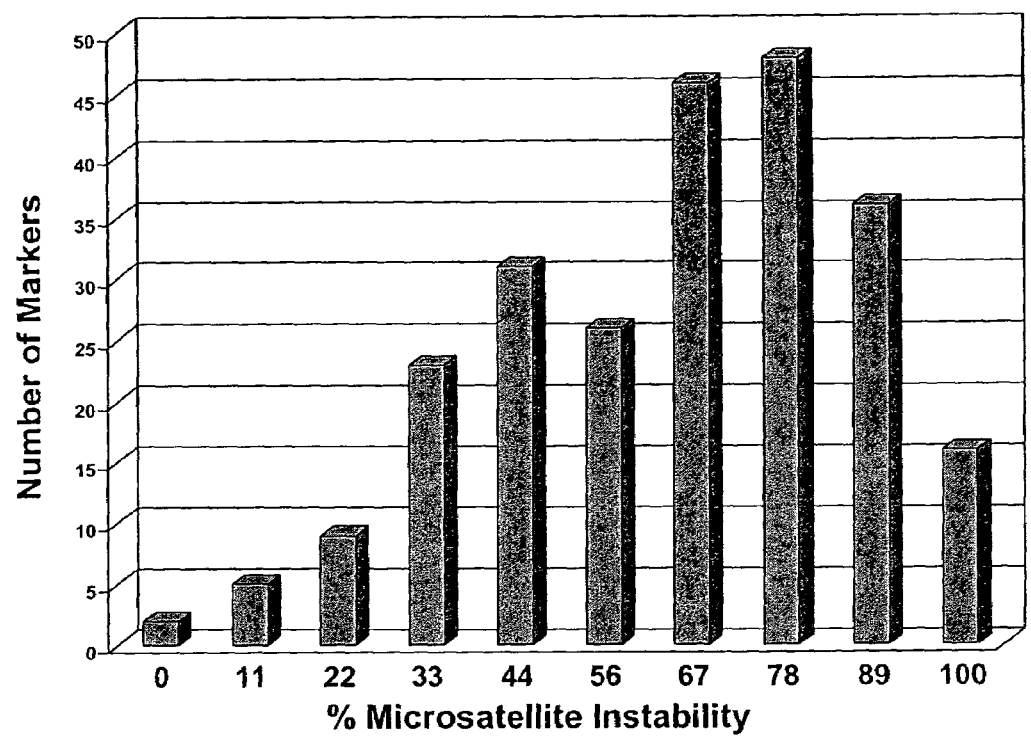
FIG. 5. Results of screening of tetranucleotide repeat markers for frequency of microsatellite instability. The figure is a plot of the number of microsatellite loci, out of a total of 273 markers, that displays a given percent MSI. For example, approximately 15 loci were altered in 100% of MSI-H tumor samples evaluated.
Figure 6:
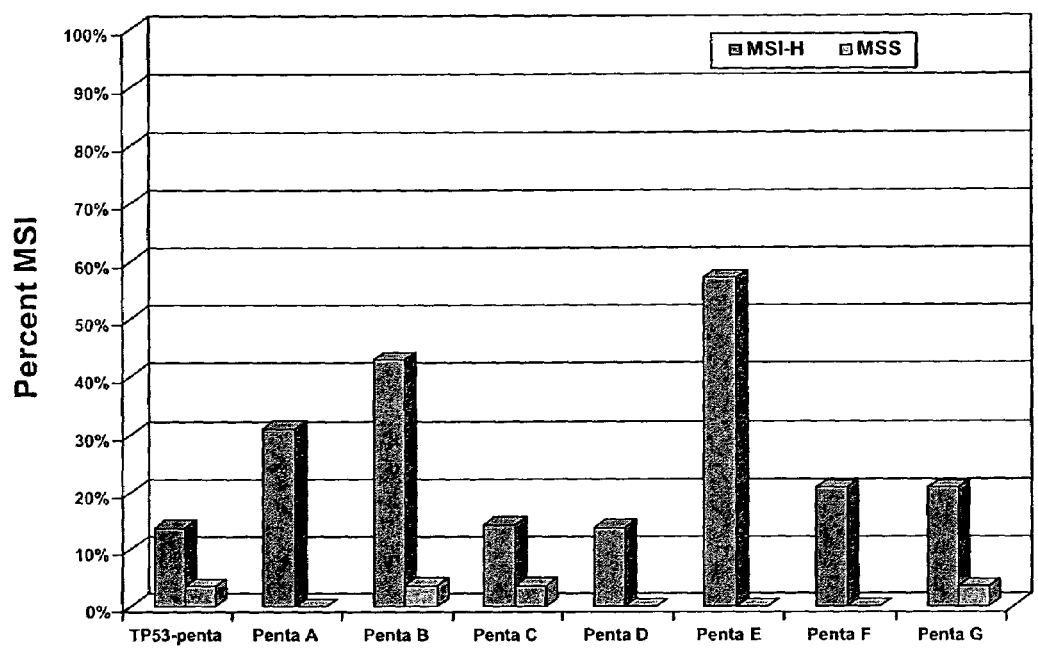
FIG. 6. Results of screening of pentanucleotide repeat markers for frequency of microsatellite instability. The figure is a plot of the percent MSI observed for each of eight different tetra-nucleotide repeat loci in a set of nine MSI-H and a set of 30 MSS tumors.

The tetra- and penta-nucleotide repeat loci exhibited the smallest amount of stutter of the loci screened, above. See FIG. 4 for a plot of the % stutter results observed at the tetra- and penta-nucleotide repeat loci. The tetra-nucleotide repeat markers also varied in frequency of alteration, ranging from 0 to 100% MSI in the MSI-H group (FIG. 5). Penta-nucleotide markers, in general, displayed low levels of MSI (FIG. 6). Microsatellite markers showing high sensitivity to MSI (>88% MSI with MSI-H samples) and high specificity (<8% MSI with MSI-L and MSS samples) with the CHTN samples were selected for further evaluation with 20 additional normal/tumor colon cancer samples from Mayo Clinic (Rochester, Minn.) (see Example 5).

EXAMPLE 2

Identification and Characterization of Mono-nucleotide Repeat Loci

Due to the highly informative nature of mono-nucleotide repeat loci in determining MSI phenotype, we also investigated poly (A) regions of the human genome as a new source of markers for MSI assays. To accomplish this, mono-nucleotide repeats were identified from GenBank using BLASTN (Altschul, et al. 1990 *J. Mol. Biol.* 215:402-410) searches for $(A)_{30}(N)_{30}$ sequences. The $(N)_{30}$ sequence was added to eliminate frequent mRNA hits and to assure that flanking sequence was available for designing primers for PCR. Next, flanking primers were designed for 33 GenBank DNA sequences using Oligo Primer Analysis Software version 6.0 (National Biosciences, Inc., Plymouth, Minn.) to amplify the region containing the poly (A) repeat. Evaluation of loci was performed using 9 MSI-H and 30 MSS colon cancer samples and corresponding normal DNA samples. Protocols for PCR, detection and analysis are described in Example 1.

Figure 7:
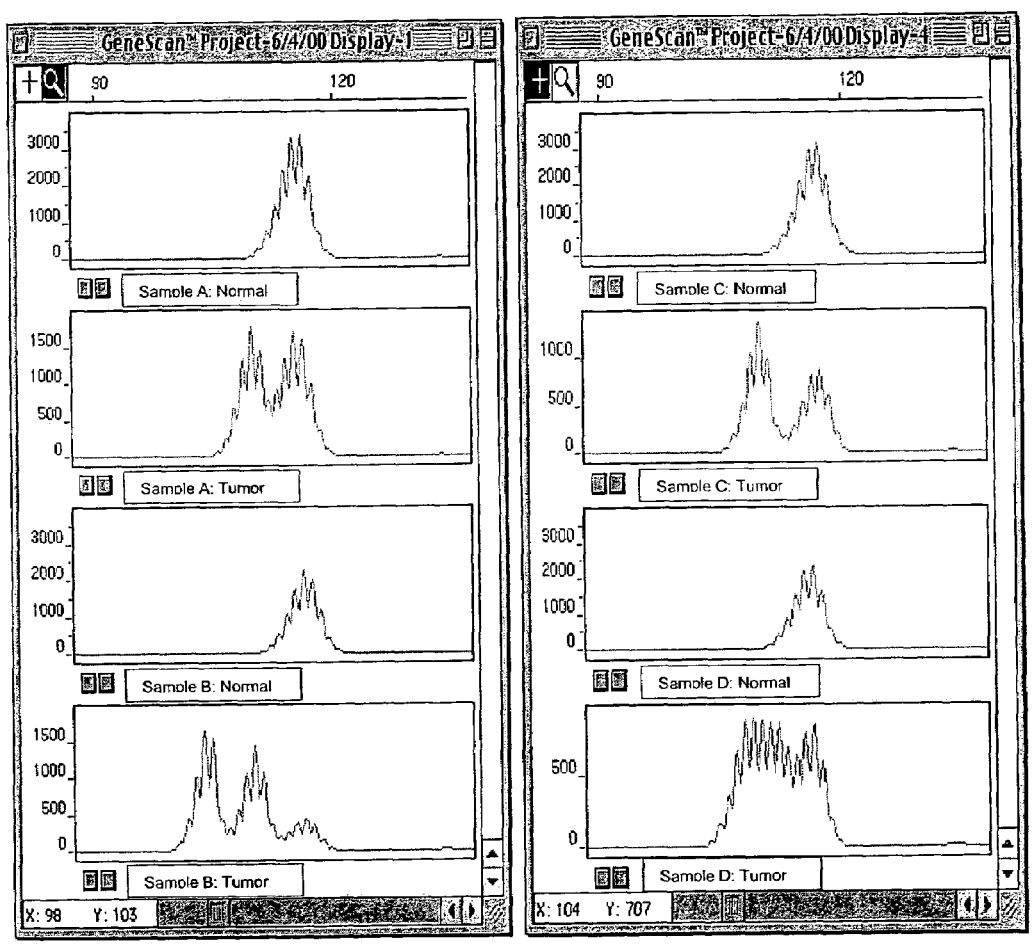
FIG. 7. Microsatellite instability analysis using MONO-15 marker. The figure is a plot generated from capillary electrophoresis products of amplification of the MONO-15 locus of DNA from four different sets of paired normal and tumor samples originating from four different individuals.

Two characteristics were screened for in the new loci. First, loci were screened for which could detect MSI in the MSI-H group and not in the MSS group. Secondly, loci were selected on the basis of being monomorphic or nearly monomorphic (quasi-monomorphic). The monomorphic nature of the new loci was determined by genotyping 96 samples from 5 racial groups (African-American, Asian-American, Caucasian-American, Hispanic-American, Indian-American). Screening of 33 mono-nucleotide repeat loci revealed four new mono-nucleotide repeat loci (MONO-3, MONO-11, MONO-15, and MONO-19) that displayed high sensitivity to MSI (Table 4 and FIG. 7) and were relatively homozygous and monomorphic (Table 5). The degree of homozygosity and mono morphism detected at each such locus is shown on Table 6.

TABLE 4

Results from Screening of Mono-nucleotide Repeat Loci

| MSI Type | BAT-25 | BAT-26 | MONO-3 | MONO-11 | MONO-15 | MONO-19 |
|---|---|---|---|---|---|---|
| MSI-H | 100% | 100% | 100% | 100% | 100% | 100% |
| MSI-L or MSS | 0% | 0% | 0% | 0% | 0% | 0% |

TABLE 5

Polymorphism Level of Mono-nucleotide Repeat Loci

| | BAT-25 | BAT-26 | MONO-11 | MONO-15 |
|---|---|---|---|---|
| % Homozygosity | 95% (82/86) | 95% (89/94) | 89% (76/85) | 99% (87/88) |
| % Monomorphic | 95% | 95% | 89% | 99% |

EXAMPLE 3

Population Studies

A population study was conducted in which 93 samples from African-American individuals were genotyped using preferred microsatellite loci selected as candidates for multiplexing in the studies illustrated in Examples 1 and 2, above. See Table 6, below, and Table 3, above, for the amplification conditions used. See Table 7, below, for a list of the loci amplified and analyzed in this study. In addition, a pooled Human Diversity DNA sample and control CEPH DNAs 1331-1 and 1331-2 (Coriell Cell Repository, Camden, N.J.) were included in the screening population. African-American samples were used because they contain the greatest genetic diversity found in all racial groups.

To facilitate screening of 96 samples with 22 different microsatellite markers, selected markers were multiplexed in small groups of three. Multiplexed primer sets were used to amplify individual sample DNAs using conditions described below.

TABLE 6

25 µl PCR reaction

| PCR Master Mix Component | Volume Per Sample |
|---|---|
| Nuclease Free Water | 17.30 µl |
| GoldST★R 10X Buffer (Promega) | 2.50 µl |
| 10X Triplex Primer Mix (1 to 10 µM each) | 2.50 µl |
| AmpliTaq Gold DNA Polymerase (5 Units/µl) (Perkin Elmer) | 0.20 µl |
| Template DNA (0.4 ng/µl) | 2.50 µl |
| Total Reaction Volume | 25.00 µl |

The results of the population study are summarized in Table 7. The size of the smallest and largest allele for each locus was identified to determine allele size range. To calculate percent stutter, the peak height of the stutter band was divided by the peak height generated by the true allele, then multiplied by 100. Minimum and maximum stutter values were calculated for each locus as well as the combined average percent stutter from 20 random samples.

TABLE 7

Summary of Results of Population Study

| | | Allele Size Range | | Average |
|---|---|---|---|---|
| Locus | GenBank ID # | GenBank | Pop Study | % Stutter |
| BAT-25 | U63834 | 18 bp | 42 bp | ND |
| BAT-26 | U41210 | 18 bp | 12 bp | ND |
| MONO-11 | AC007684 | ND | 14 bp | ND |
| MONO-15 | AC007684 | ND | 6 bp | ND |
| D1S547 | G07828 | 46 bp | 26 bp | 4.9 |
| D1S518 | G07854 | 48 bp | ND | ND |
| D1S1677 | G09926 | 40 bp | 35 bp | 9.7 |
| D2S1790 | G08190 | 68 bp | 44 bp | 7.8 |
| D3S2432 | G08240 | 67 bp | 40 bp | 8.0 |
| D5S818 | G08446 | 36 bp | ND | ND |
| D5S2849 | G15752 | 40 bp | 37 bp | 5.5 |
| D6S1053 | G08556 | 48 bp | 36 bp | 6.9 |
| D7S1808 | G08643 | 58 bp | 44 bp | 7.6 |
| D7S3046 | G10353 | 48 bp | 71 bp | 12.9 |
| D7S3070 | G27340 | 44 bp | 44 bp | 10.3 |
| D8S1179 | G08710 | 44 bp | ND | ND |
| D9S2169 | G08748 | 12 bp | ND | ND |
| D10S677 | G12433 | 28 bp | 40 bp | 5.5 |
| D10S1426 | G08812 | 28 bp | ND | ND |
| D10S2470 | G10285 | 48 bp | 29 bp | 5.9 |
| D12S391 | G08921 | 52 bp | 48 bp | 7.6 |
| D17S1294 | G07967 | 44 bp | 28 bp | 7.2 |
| D17S1299 | G07952 | 40 bp | ND | ND |
| D18S51 | L18333 | 76 bp | ND | ND |
| FGA | M64982 | 120 bp | ND | ND |

EXAMPLE 4

MSI Multiplex Design

In order to develop a multiplex MSI assay system which is highly sensitive to MSI, with minimal stutter, and minimal incidence of LOH, the criteria listed in Table 8, below, were used to screen loci identified in the Examples above as possible candidates for use in MSI analysis:

TABLE 8

MSI Loci Specifications for Use in Multiplex

| | |
|---|---|
| Monoplex specifications | |
| Tetra-nucleotides | >70% MSI in MSI-H samples |
| | <8% MSI with MSI-L and MSS samples |
| | LOH <14% in MSI-H samples |
| | Average % Stutter <13% |
| Mono-nucleotides | 100% MSI in MSI-H samples |
| | 0% MSI with MSI-L and MSS samples |
| Multiplex specifications | 9 loci; 3 mono- and 6 tetra-nucleotides |
| | All amplicons <250 bp |
| | Robust amplification of DNA from PET samples |
| | Robust amplification of 1 to 2 ng DNA |
| | Balanced peak heights between all loci in multiplex |
| | Sensitivity >99.9% |
| | Specificity >99.9% |

The loci listed in Table 9, below, were identified as loci meeting the specifications listed in Table 8, above.

TABLE 9

Preferred Microsatellite Loci for Multiplexing

| Locus | Repeat Type | GenBank Accession No. | Primer SEQ. ID. | % MSI (MSI-H) | % LOH (MSI-H) | % MSI (MSS or MSI-L) |
|---|---|---|---|---|---|---|
| BAT-25 | Mono | U63834 | 1, 2 | 100% | 0% | 0% |
| BAT-26 | Mono | U41210 | 3, 4 | 100% | 0% | 0% |
| MONO-11 | Mono | AC007684 | 5, 6 | 100% | 0% | 0% |
| MONO-15 | Mono | AC007684 | 7, 8 | 100% | 0% | 0% |
| D1S518 | Tetra | G07854 | 9, 10 | 83% | 0% | 0% |
| D1S547 | Tetra | G07828 | 11, 12 | 78% | 3% | 0% |
| D1S1677 | Tetra | G09926 | 13, 14 | 80% | 0% | 3% |
| D2S1790 | Tetra | G08190 | 15, 16 | 82% | 3% | 3% |
| D3S2432 | Tetra | G08240 | 17, 18 | 83% | 3% | 3% |
| D5S818 | Tetra | G08446 | 19, 20 | 72% | 14% | 3% |
| D5S2849 | Tetra | G15752 | 21, 22 | 76% | 7% | 0% |
| D6S1053 | Tetra | G08556 | 23, 24 | 76% | 0% | 0% |
| D7S1808 | Tetra | G08643 | 25, 26 | 90% | 0% | 0% |
| D7S3046 | Tetra | G10353 | 27, 28 | 93% | 0% | 0% |
| D7S3070 | Tetra | G27340 | 29, 30 | 86% | 3% | 3% |
| D8S1179 | Tetra | G08710 | 31, 32 | 75% | 7% | 7% |
| D9S2169 | Tetra | G08748 | 33, 34 | 72% | 3% | 0% |
| D10S1426 | Tetra | G08812 | 35, 36 | 86% | 3% | 0% |
| D10S2470 | Tetra | G10285 | 37, 38 | 83% | 3% | 0% |
| D12S391 | Tetra | G08921 | 39, 40 | 79% | 3% | 0% |
| D17S1294 | Tetra | G07967 | 41, 42 | 86% | 3% | 0% |
| D17S1299 | Tetra | G07952 | 43, 44 | 79% | 3% | 0% |
| D18S51 | Tetra | L18333 | 45, 46 | 75% | 7% | 0% |
| FGA | Tetra | M64982 | 47, 48 | 82% | 7% | 7% |

* MSI-H samples: N = 29 and MSI-L/S samples N = 30.

EXAMPLE 5

Analysis of Mismatch Repair Genes

In order to determine the underlying cause of MSI in MSI-H tumor samples used in developing the Multiplex MSI Assay, protein expression levels for MLH1 and MSH2 genes were examined. Immunohistochemical analysis of paraffin-embedded tissues from eight MSI-H samples was performed as described in Thibodeau et al. (*Cancer Research* 58, 1713-1718). Lack of protein expression in MLH1 and MSH2 genes is expected in tumor samples exhibiting high levels of MSI and is an indication of dysfunctional mismatch repair system.

The results of the immunohistochemical assays on the MSI-H tumor samples is shown in Table 10.

TABLE 10

Protein Expression of MSH1 And MSH2 in MSI-H Cancer Samples

| Tumor Sample | MSI | | Protein expression | |
|---|---|---|---|---|
| | Source | Phenotype | HMLH1 | HMSH2 |
| C172 | CHTN | MSI-H | − | + |
| C404 | CHTN | MSI-H | − | + |
| C507 | CHTN | MSI-H | − | + |
| C546 | CHTN | MSI-H | − | + |
| C624 | CHTN | MSI-H | ND | ND |
| C710 | CHTN | MSI-H | − | + |
| C1166 | CHTN | MSI-H | − | + |
| C5412 | CHTN | MSI-H | − | + |
| S15945 | CHTN | MSI-H | + | + |
| A-1 | Mayo Clinic | MSI-H | − | + |
| A-5 | Mayo Clinic | MSI-H | − | + |
| A-7 | Mayo Clinic | MSI-H | + | − |
| A-15 | Mayo Clinic | MSI-H | − | + |
| A-19 | Mayo Clinic | MSI-H | − | + |
| A-29 | Mayo Clinic | MSI-H | − | + |

TABLE 10-continued

Protein Expression of MSH1 And MSH2 in MSI-H Cancer Samples

| Tumor Sample | MSI Source | Phenotype | Protein expression HMLH1 | HMSH2 |
|---|---|---|---|---|
| A-49 | Mayo Clinic | MSI-H | + | − |
| A-50 | Mayo Clinic | MSI-H | − | + |
| A-73 | Mayo Clinic | MSI-H | − | + |
| A-102 | Mayo Clinic | MSI-H | + | − |
| B-2 | Mayo Clinic | MSI-H | − | + |
| B-52 | Mayo Clinic | MSI-H | − | + |
| B-61 | Mayo Clinic | MSI-H | − | + |
| B-75 | Mayo Clinic | MSI-H | − | + |
| B-76 | Mayo Clinic | MSI-H | − | + |
| B-93 | Mayo Clinic | MSI-H | − | + |
| B-107 | Mayo Clinic | MSI-H | − | + |
| B-155 | Mayo Clinic | MSI-H | − | + |
| B-164 | Mayo Clinic | MSI-H | − | + |
| B-166 | Mayo Clinic | MSI-H | − | + |
| B-173 | Mayo Clinic | MSI-H | − | + |
| B-199 | Mayo Clinic | MSI-H | − | + |
| B-209 | Mayo Clinic | MSI-H | − | + |
| B-210 | Mayo Clinic | MSI-H | − | + |
| B-268 | Mayo Clinic | MSI-H | − | + |
| B-299 | Mayo Clinic | MSI-H | − | + |
| B-334 | Mayo Clinic | MSI-H | − | + |
| B-379 | Mayo Clinic | MSI-H | − | + |
| B-402 | Mayo Clinic | MSI-H | − | + |
| B-564 | Mayo Clinic | MSI-H | − | + |

EXAMPLE 6

MSI Multiplex Assay Development and Validation

Once the best loci were selected for use in designing multiplexes to be analyzed according to the methods of the present invention, problems associated with multiplex PCR and incompatibility between loci needed to be overcome. This required careful primer design and extensive trial and error to find loci that were capable of simultaneous amplification using a single set of PCR conditions. Problems encountered included: (1) primer-primer interactions that occurred when large number of oligos were combined in a single PCR reaction, (2) primer design limitations due to sequence constraints at a particular locus (e.g., minimum size of amplicon allowed by DNA sequence, sub-optimal % GC of primers, difficulty balancing Tm's for all primers under uniform PCR conditions, difficulty in finding primers with desirable thermal profiles to minimize non-specific amplification, hairpin formation and self dimerization of primers, homology to other repeat sequences in human genome), and (3) multiplex design allowing separation of all 9 loci within limited size range of 250 bp.

Figure 8:
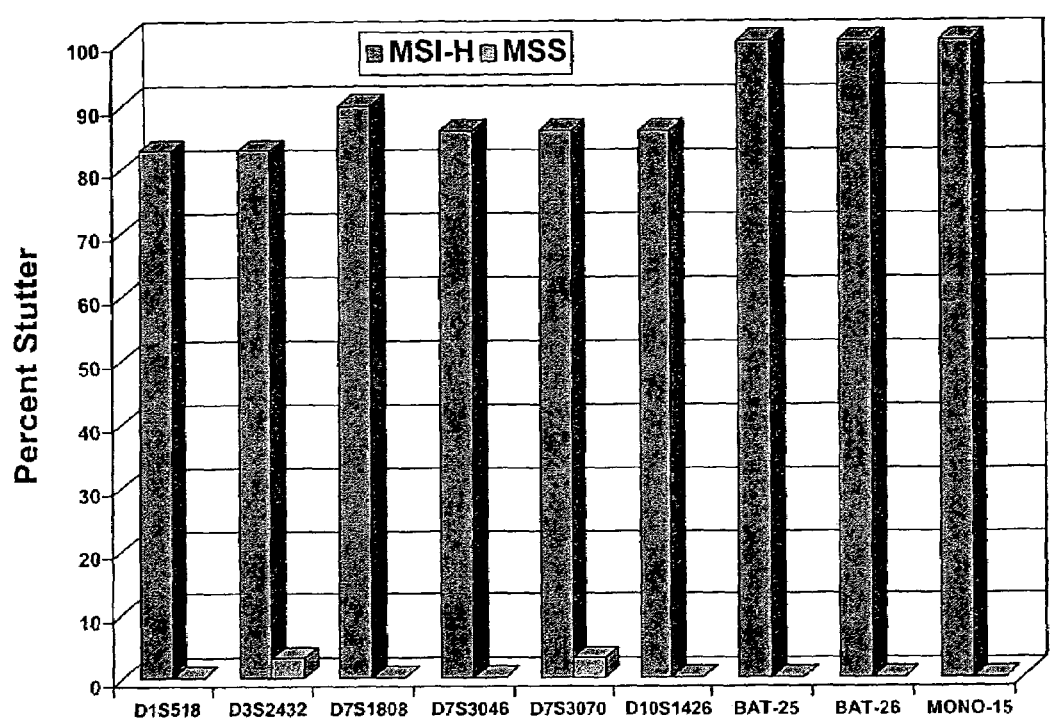
FIG. 8. Percent MSI in 59 colon cancer samples using nine-locus MSI multiplex. The figure is a plot of the percent MSI observed in 59 colon cancer samples (29 MSH and 30 MSI-L or MSS samples) using a nine locus MSI multiplex (D1S518, D3S2432, D7S1808, D7S3046, D7S9070, D10S1426, BAT-25, BAT-26, and MONO-15.

Based on extensive evaluation of close to 300 microsatellite markers described in Examples 1 through 5, nine loci were selected for the preferred MSI Multiplex Assay (Table 11). Three loci are monoplex repeats (BAT-25, BAT-26 and MONO-15) and six were tetra-nucleotide repeats (D7S3046, D10S1426, D10S2470, D7S3070, D17S1294, D7S1808). These loci represent the best known set of loci known for determining MSI in tumor samples. Results of MSI analysis on 29 MSI-H and 30 MSI-L or MSS colon cancer samples using the preferred nine-locus multiplex are summarized in FIG. 8.

Figure 9:
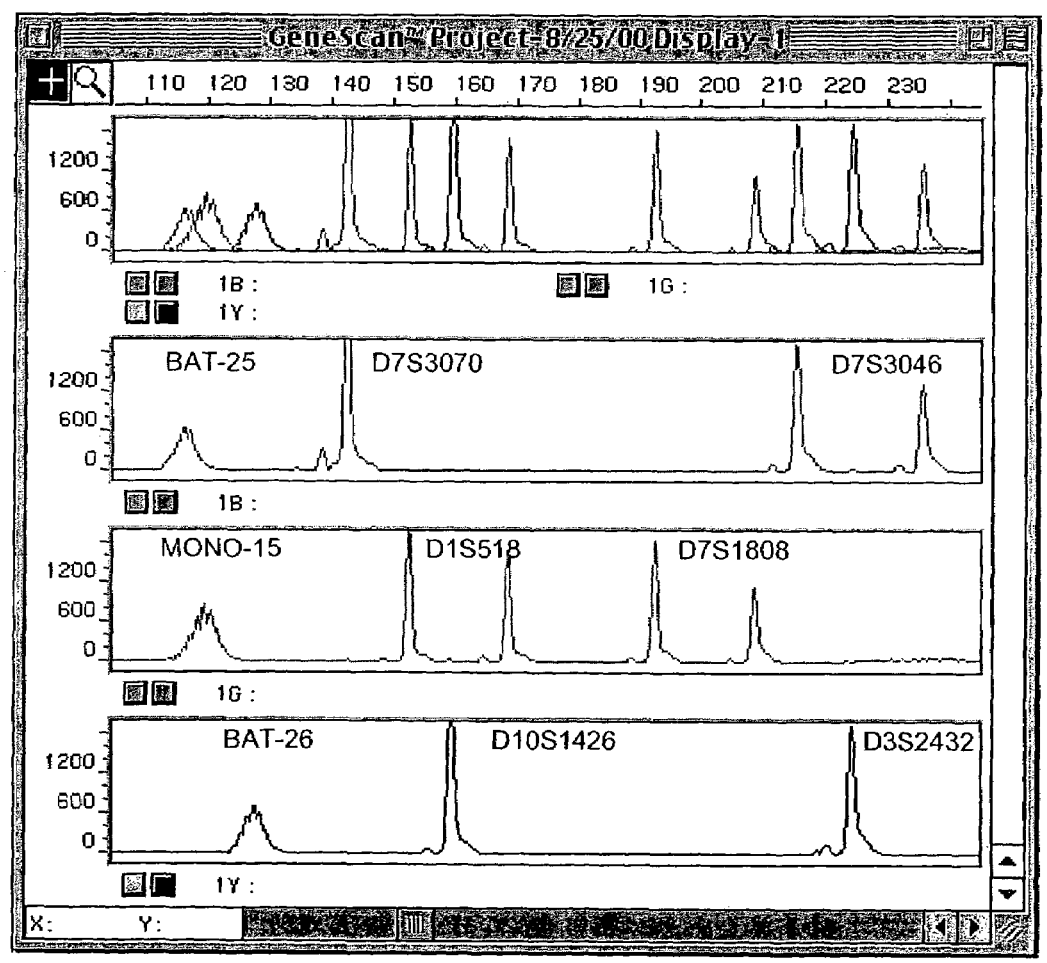
FIG. 9. Fluorescent multiplex microsatellite analysis using nine-locus MSI Multiplex. The figure is a plot generated from capillary electrophoresis of products of multiplex amplification of normal non-cancerous human genomic, using the nine locus MSI multiplex used in FIG. 8.

A typical example of MSI Multiplex is shown in FIG. 9. The image was generated by simultaneous amplifying all nine selected microsatellite loci followed by separation of PCR products on an ABI 310 CE. Separation of all nine microsatellite loci in a single capillary (or gel lane) was accomplished by designing the multiplex so that loci would not overlap in size or through use of different fluorescent dyes. The size ranges for the different multiplex loci were determined by genotyping 93 samples from African-American individuals using MSI Multiplex described following protocol described below. In addition, a pooled Human Diversity DNA sample and control CEPH DNAs 1331-1 and 1331-2 (Cornell Cell Repository) were included in the screening population. African-American samples were used because they contain the greatest amount of genetic diversity found in all racial groups.

TABLE 11

MSI Multiplex Assay Loci and Primers

| Locus | GenBank ID No. | Repeat Type | Dye | Size Range | Primer 1 (SEQ. ID.) | Primer 2 (SEQ. ID.) |
|---|---|---|---|---|---|---|
| BAT-25 | U63834 | Mono | TMR | 118–127 | 1 | 60 |
| D10S1426 | G08812 | Tetra | TMR | 152–173 | 57 | 58 |
| D3S2432 | G08240 | Tetra | TMR | 198–234 | 17 | 59 |
| BAT-26 | U41210 | Mono | FL | 103–116 | 61 | 62 |
| D7S3046 | G10353 | Tetra | FL | 122–163 | 55 | 56 |
| D7S3070 | G27340 | Tetra | FL | 186–249 | 53 | 54 |
| MONO-15 | AC007684 | Mono | JOE | 115–117 | 7 | 8 |
| D1S518 | G07854 | Tetra | JOE | 136–178 | 49 | 50 |
| D7S1808 | G08643 | Tetra | JOE | 190–218 | 51 | 52 |

Protocol for MSI Multiplex Assay. Template DNA from normal and tumor tissues obtained from same individual were purified using QIAamp Blood and Tissue Kit (QIAGEN, Santa Clarita, Calif.) following manufactures protocol. Two nanograms of template DNA in a 25 μl reaction volume was PCR amplified using protocol detailed in Table 12, below, using the cycling profile described in Table 3, above.

TABLE 12

Amplification Mix for MSI Multiplex Assay

| PCR Master Mix Component | Volume Per Sample |
|---|---|
| Nuclease Free Water | 17.00 μl |
| GoldST★R 10X Buffer (Promega) | 2.50 μl |
| Primer Pair Mix (10 μM) | 2.50 μl |
| AmpliTaq Gold DNA Polymerase (Perkin Elmer) | 0.50 μl |
| Template DNA (0.8 ng/μl) | 2.50 μl |
| Total Reaction Volume | 25.00 μl |

One microliter of PCR product was combined with 1 μl of Internal Lane Standard (Promega Corporation, Madison, Wis.) and 24 μl deionized formamide. Samples were denatured by heating at 95° C. for 3 minutes and immediately chilled on ice for 3 minutes. Separation and detection of amplified fragments was performed on an ABI PRISM 310 Genetic Analyzer following the standard protocol recommended in the User's Manual with the following settings:

| Run Module: | GS STR POP4 (Filter set A) |
|---|---|
| Injection Time: | 4 seconds |
| Injection Voltage: | 15 kV |
| Run Voltage: | 15 kV |
| Run Temperature: | 60° C. |
| Run Time: | 24 minutes |

Figure 10:
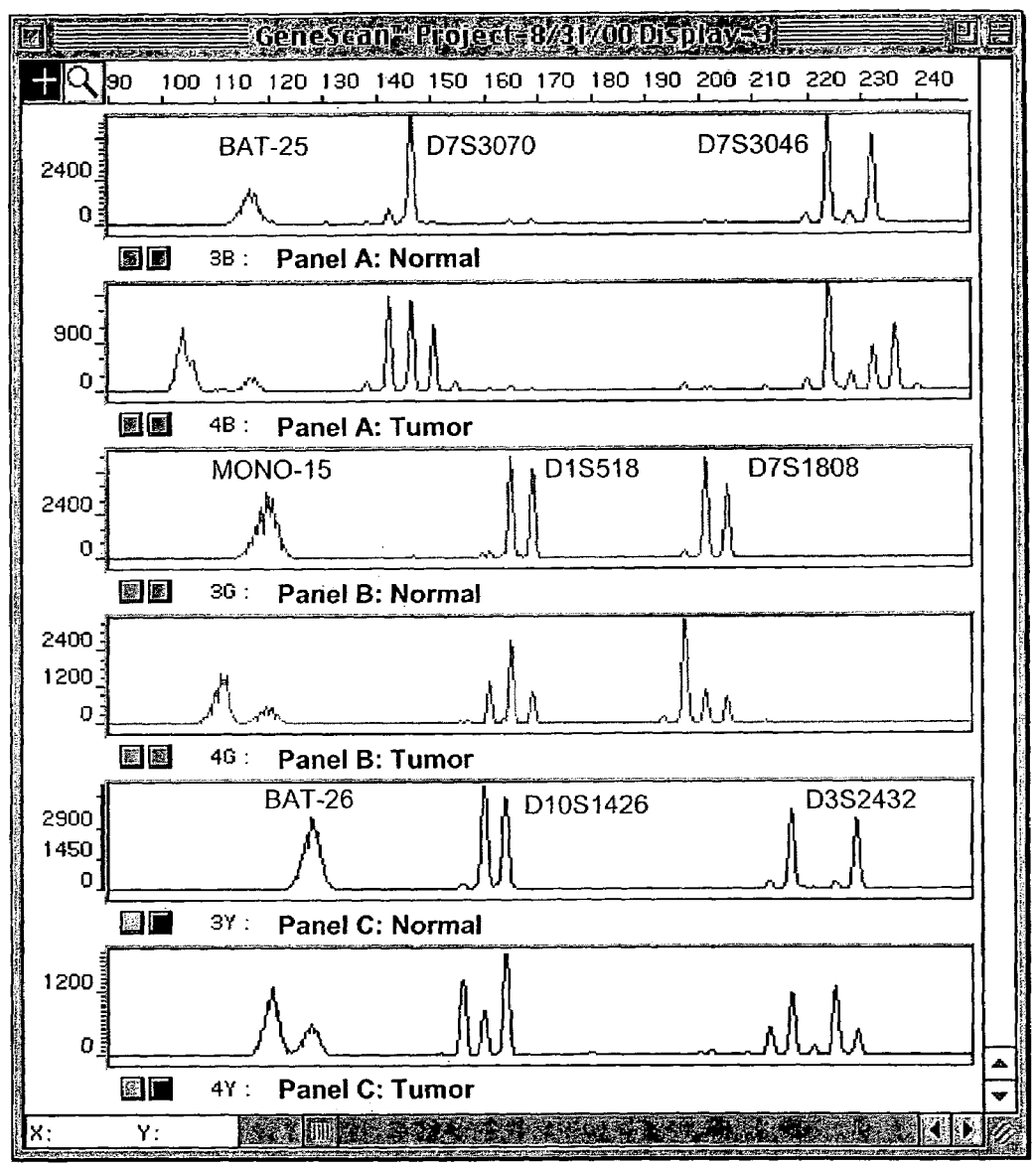
FIG. 10. Detection of microsatellite instability in colon cancer samples using nine-locus MSI multiplex. The figure is a plot generated from capillary electrophoresis of products of multiplex amplification of DNA from paired normal and colon tumor sample, using the nine locus MSI multiplex used in FIG. 8.
Figure 11:
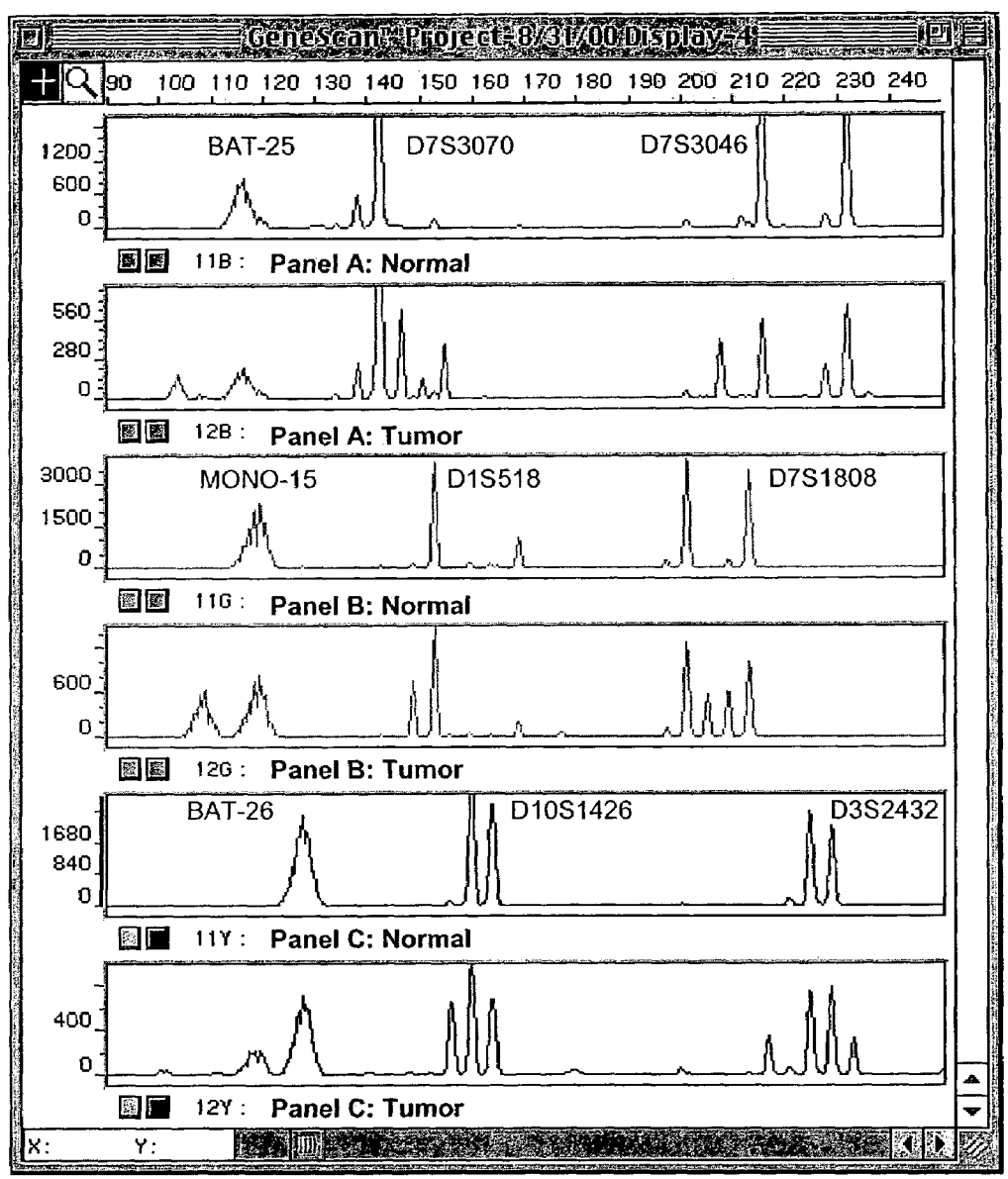
FIG. 11. Detection of microsatellite instability in colon cancer samples using nine-locus MSI multiplex is the same type of plot shown in FIG. 10, generated using a different sample of paired normal and colon cancer DNA from a different individual.
Figure 12:
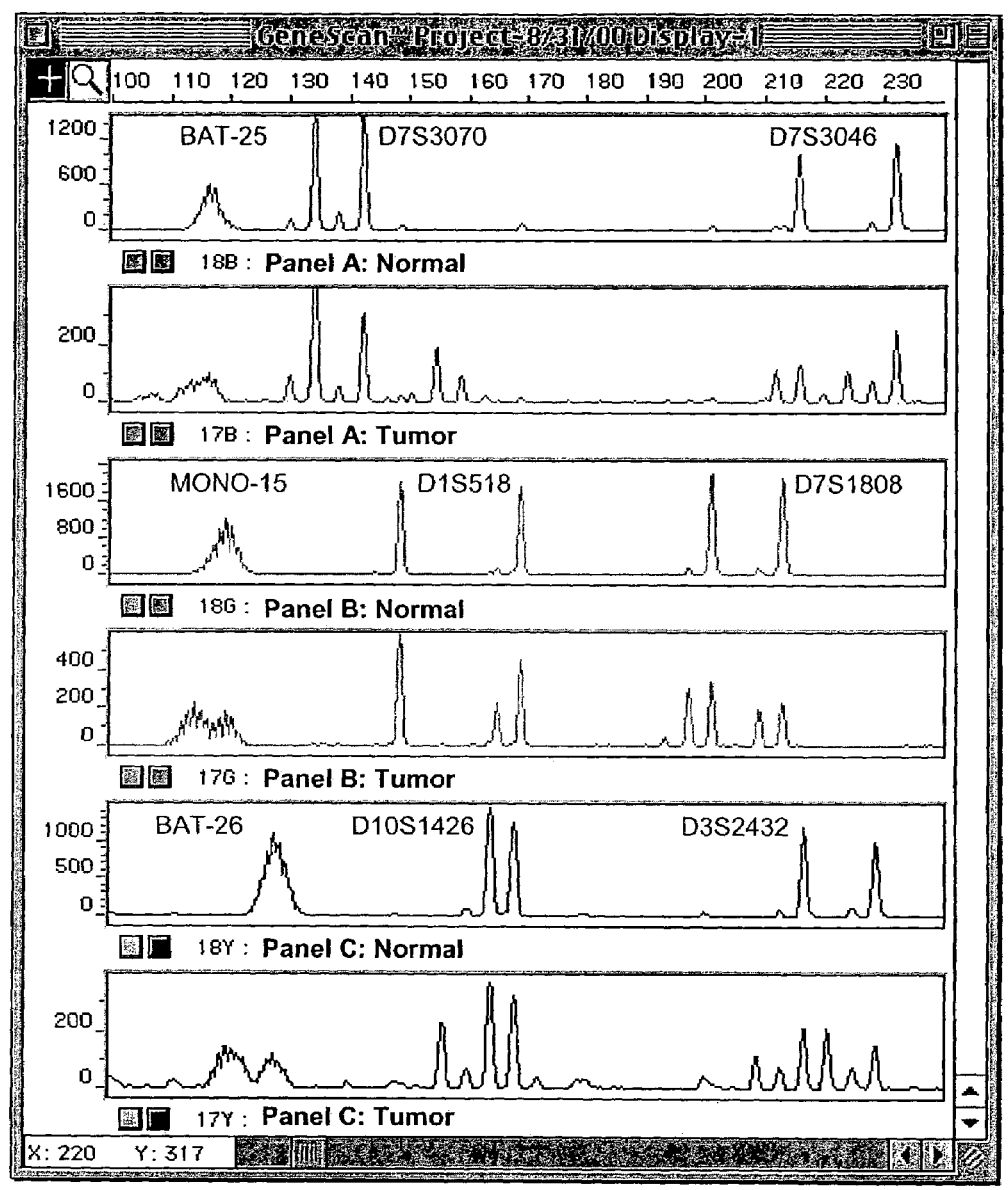
FIG. 12. Detection of microsatellite instability in stomach cancer samples using nine-locus MSI multiplex. The figure is a plot generated from capillary electrophoresis of products of multiplex amplification of DNA from paired normal and stomach cancer tumor samples, using the nine locus MSI multiplex described in FIG. 8.

Identification of normal and tumor allele amplicon sizes was accomplished by examining the appropriated electropherogram from the ABI PRISM 310 Genetic Analyzer and determining the predominate peaks for each locus. One or two peaks or alleles were present for each locus in normal samples depending upon whether individual was homozygous or heterozygous for a particular marker. Allelic patterns or genotypes for normal and tumor pairs were compared and scored as MSI positive if one or more different alleles were present in the tumor DNA samples that were not found in normal sample from the same individual. Typical examples of results obtained using multiplex designed for MSI analysis are shown in FIGS. 10 and 11 for colon cancer and FIG. 12 for stomach cancer.

EXAMPLE 7

Amplification of DNA from PET Samples Using MSI Multiplex

Figure 13:
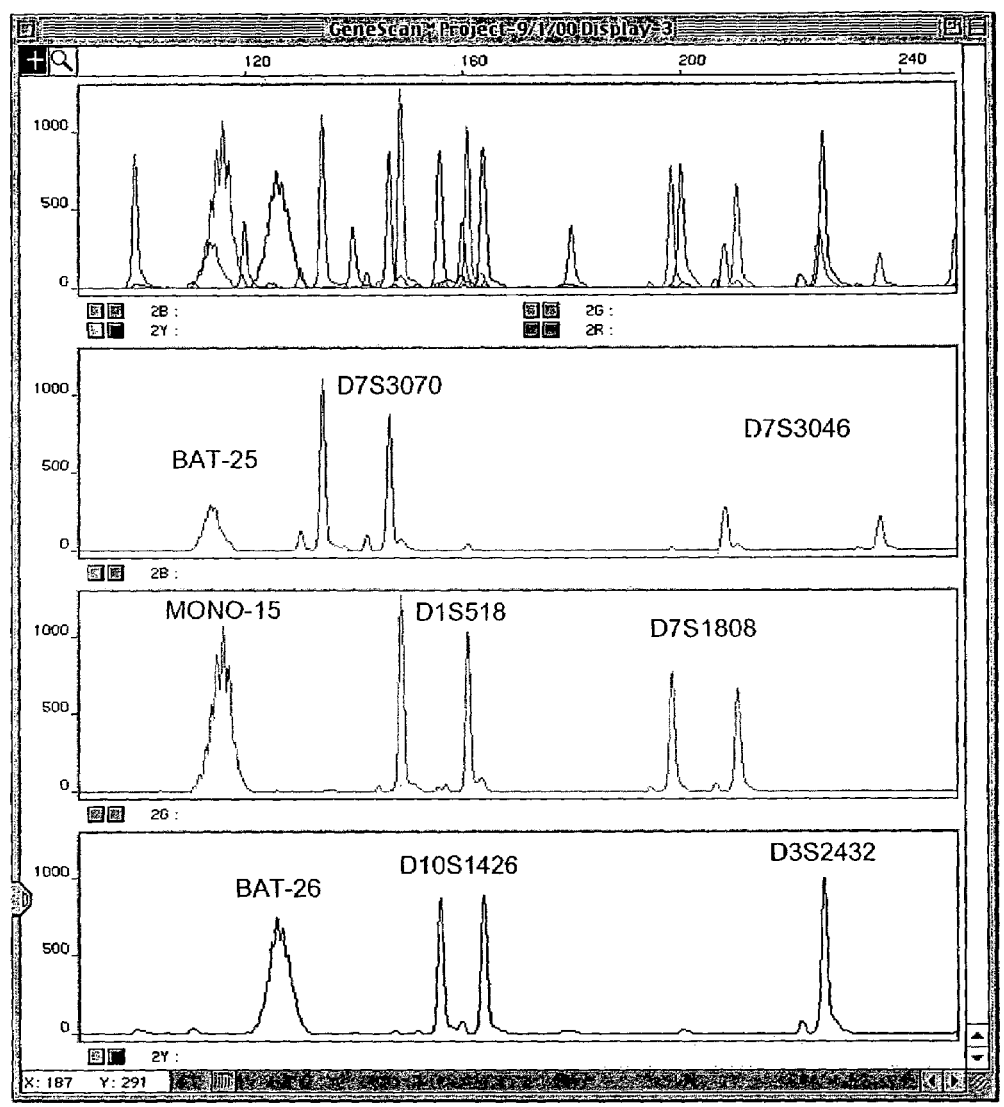
FIG. 13. Microsatellite analysis of paraffin embedded tissues with nine-locus MSI multiplex. The figure is a plot generated from capillary electrophoresis of products of multiplex amplification of DNA from paraffin embedded tissue, using the nine locus MSI multiplex described in FIG. 8.

Microsatellite loci selected for the preferred multiplex were evaluated for their ability to amplify DNA from formalin-fixed paraffin-embedded samples. DNA was extracted from three 10 micron sections cut from PET blocks using QIAamp Tissue Kit (Qiagen, Santa Clarita, Calif.) according to the manufacture's instructions with the following modifications. One hundred microliters of QIAGEN AE buffer preheated to 70° C. was added to column, incubated for 5 minutes, centrifuged, then reapplied to column for second elution. Two microliters (out of 100 µl) of purified DNA solution was used as template for PCR reactions. The nine locus multiplexed primer set described in Example 6 was used to amplify DNA from PET samples. The results indicate that the MSI Multiplex is capable of amplifying DNA from difficult and commonly used PET samples (FIG. 13).

While the present invention has now been described and exemplified with some specificity, those skilled in the art will appreciate the various modifications, including variations, additions, and omissions that may be made in what has been described. Accordingly, it is intended that these modifications also be encompassed by the present invention and that the scope of the present invention be limited solely by the broadest interpretation that lawfully can be accorded the appended claims.

We claim:

1. A method of detecting microsatellite instability in a DNA sample comprising:
   a) co-amplifying a set of microsatellite loci of the DNA sample to produce amplified DNA fragments, the set of loci comprising at least one tetranucleotide repeat locus selected from the group consisting of D1S518, D1S547, D1S1677, D2S1790, D3S2432, D5S2849, D6S1053, D7S3046, D7S1808, D7S3070, D9S2169, D10S1426, D10S2470, D12S391, and D17S1294 wherein the DNA sample is from tumor cells, from cells suspected of being cancerous, or from other biological material suspected of being cancerous;
   b) determining the size of the amplified DNA fragments; and
   c) comparing the size of the amplified DNA fragments of step b) to the size of corresponding amplified DNA fragments from a paired normal DNA sample, a difference in size between one or more DNA fragments between the samples being indicative of microsatellite instability.

2. The method of claim 1, wherein the set of microsatellite loci comprises at least two tetranucleotide repeat loci selected from the group consisting of D1S518, D1S547, D1S1677, D2S1790, D3S2432, D5S2849, D6S1053, D7S3046, D7S1080, D7S3070, D9S2169, D10S1426, D10S2470, D12S391, and D17S1294.

3. The method of claim 1, wherein the set of microsatellite loci comprises at least three tetranucleotide repeat loci selected from the group consisting of D1S518, D1S547, D1S1677, D2S1790, D3S2432, D5S2849, D6S1053, D7S3046, D7S1808, D7S3070, D9S2169, D10S1426, D10S2470, D12S391, and D17S1294.

4. The method of claim 1, wherein the set of microsatellite loci comprises D1S518, D3S2432, D7S1808, D7S3046, D7S3070 and D10S1426.

5. The method of claim 1, wherein the microsatellite loci further comprises at least one mononucleotide repeat locus.

6. The method of claim 1, wherein the set of microsatellite loci is a set of at least five micro satellite loci, comprising:
   at least two mononucleotide repeat loci selected from the group consisting of BAT-25, BAT-26, MONO-11, and MONO-15; and
   at least three tetranucleotide repeat loci selected from the group consisting of FGA, D1S518, D1S547, D1S1677, D2S1790, D3S2432, D5S818, D5S2849, D6S1053, D7S3046, D7S1808, D7S3070, D8S1179, D9S2169, D10S1426, D10S2470, D12S391, D17S1294, D17S1299, and D18S551.

7. The method of claim 4, wherein the tetranucleotide repeat loci are amplified using oligonucleotide primers comprising SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:17 and SEQ ID NO:59.

* * * * *

UNITED STATES PATENT AND TRADEMARK OFFICE
CERTIFICATE OF CORRECTION

PATENT NO.         : 7,364,853 B2
APPLICATION NO. : 11/037321
DATED              : April 29, 2008
INVENTOR(S)      : Jeffery W. Bacher et al.

Page 1 of 1

It is certified that error appears in the above-identified patent and that said Letters Patent is hereby corrected as shown below:

Column 45, Claim 2, line 8, "D7S1080" should read --D7S1808--.

Column 46, Claim 6, line 2, "micro satellite" should read --microsatellite--.

Column 46, Claim 6, line 11, "D18S551" should read --D18S51--.

Signed and Sealed this

Twenty-fifth Day of August, 2009

David J. Kappos
*Director of the United States Patent and Trademark Office*